US009380964B2

(12) United States Patent
Hagino et al.

(10) Patent No.: US 9,380,964 B2
(45) Date of Patent: Jul. 5, 2016

(54) DEVICE FOR INTERSTITIAL FLUID EXTRACTION, PRODUCTION PROCESS THEREOF AND ANALYZING PROCESS OF INTERSTITIAL FLUID USING THE DEVICE

(71) Applicants: Sysmex Corporation, Hyogo (JP); Nichiban Co., Ltd., Tokyo (JP)

(72) Inventors: Kei Hagino, Hyogo (JP); Junko Kojima, Hyogo (JP); Akihito Takezaki, Tokyo (JP); Reona Koike, Tokyo (JP); Kazuki Isobe, Tokyo (JP)

(73) Assignees: NICHIBAN CO., LTD., Tokyo (JP); SYSMEX CORPORATION, Hyogo (JP)

( * ) Notice: Subject to any disclaimer, the term of this patent is extended or adjusted under 35 U.S.C. 154(b) by 271 days.

(21) Appl. No.: 13/975,854

(22) Filed: Aug. 26, 2013

(65) Prior Publication Data

US 2013/0345597 A1    Dec. 26, 2013

Related U.S. Application Data

(62) Division of application No. 12/849,108, filed on Aug. 3, 2010, now abandoned.

(30) Foreign Application Priority Data

Aug. 4, 2009    (JP) .................................. 2009-181883
Jun. 24, 2010   (JP) .................................. 2010-143752

(51) Int. Cl.
*A61B 5/145* (2006.01)
*A61B 10/00* (2006.01)

(Continued)

(52) U.S. Cl.
CPC ........... *A61B 5/14514* (2013.01); *A61B 5/1455* (2013.01); *A61B 5/14532* (2013.01);
(Continued)

(58) Field of Classification Search
CPC ........... A61B 5/14514; A61B 5/14532; A61B 5/14546; A61B 10/0045
See application file for complete search history.

(56) References Cited

U.S. PATENT DOCUMENTS 4,699,146 A * 10/1987 Sieverding .............. A61L 15/58
                                                                 252/519.21
5,036,861 A    8/1991  Sembrowich et al.
(Continued)

FOREIGN PATENT DOCUMENTS

EP    0326398 A2    8/1989
JP    04-358532 A   12/1992
(Continued)

OTHER PUBLICATIONS

Office Action from corresponding Japanese Application No. 2010-143752, dated Sep. 24, 2013.
(Continued)

*Primary Examiner* — Sean Dougherty
(74) *Attorney, Agent, or Firm* — Porter, Wright, Morris & Arthur, LLP

(57) ABSTRACT

A device for interstitial fluid extraction, having a base material formed from a synthetic resin film, a pressure sensitive adhesive layer, a hydrogel layer formed from at least one hydrophilic polymer selected from the group consisting of polyvinyl alcohol and polyvinyl pyrrolidone, and a release layer, wherein the hydrogel layer has an area of a size that the pressure sensitive adhesive layer is exposed from around the hydrogel layer, does substantially not contain a sodium ion and causes no water separation.

12 Claims, 12 Drawing Sheets

(51) Int. Cl.
*A61B 5/1455* (2006.01)
*C08J 3/075* (2006.01)

(52) U.S. Cl.
CPC ......... *A61B5/14546* (2013.01); *A61B 10/0045* (2013.01); *C08J 3/075* (2013.01); *A61B 2010/008* (2013.01); *Y10T 156/10* (2015.01)

(56) References Cited

U.S. PATENT DOCUMENTS

| | | | |
|---|---|---|---|
| 5,224,927 | A | 7/1993 | Tapper |
| 5,480,717 | A | 1/1996 | Kundel et al. |
| 5,846,214 | A | 12/1998 | Makuuchi et al. |
| 8,271,064 | B2 * | 9/2012 | Brenneman ........ A61B 5/14514 600/309 |
| 2003/0113827 | A1 * | 6/2003 | Burkoth ............. A61B 5/14532 435/14 |
| 2004/0087671 | A1 * | 5/2004 | Tamada ............... A61B 5/1486 516/99 |
| 2007/0027383 | A1 * | 2/2007 | Peyser ............... A61B 5/14521 600/347 |
| 2007/0168051 | A1 * | 7/2007 | Bronnenberg et al. ......... 700/20 |
| 2007/0168851 | A1 * | 7/2007 | Hunt .............................. 715/500 |
| 2007/0168852 | A1 * | 7/2007 | Erol et al. .................. 715/500.1 |
| 2007/0168862 | A1 * | 7/2007 | Hunt .............................. 715/705 |
| 2007/0174758 | A1 * | 7/2007 | Ando et al. ................. 715/500.1 |
| 2007/0174917 | A1 * | 7/2007 | Guruswamy ................... 726/25 |
| 2007/0233011 | A1 * | 10/2007 | Hagino ................ A61B 5/1411 604/187 |

FOREIGN PATENT DOCUMENTS

| | | |
|---|---|---|
| JP | 6-178815 A | 6/1994 |
| JP | 06-315526 A | 11/1994 |
| JP | 09-262249 A | 10/1997 |
| JP | 2000-070356 A | 3/2000 |
| JP | 2003-344394 A | 12/2003 |
| WO | 96/00110 A1 | 1/1996 |
| WO | 97/02811 A1 | 1/1997 |
| WO | 03/052125 A1 | 6/2003 |

OTHER PUBLICATIONS

Extended European Search Report from the corresponding European Application No. 10171908.6 dated Nov. 5, 2012.
Notification of Decision of Grant of Patent Right from corresponding CN 201010246264.7 dated Nov. 4, 2013.

* cited by examiner

DEVICE FOR INTERSTITIAL FLUID EXTRACTION, PRODUCTION PROCESS THEREOF AND ANALYZING PROCESS OF INTERSTITIAL FLUID USING THE DEVICE

TECHNICAL FIELD

The present invention relates to a device for interstitial fluid extraction and a production process thereof, and particularly to a device for interstitial fluid extraction, which has a hydrogel layer of polyvinyl alcohol (PVA) and/or polyvinyl pyrrolidone (PVP) through a pressure sensitive adhesive layer on one surface of a base material and can be used in quantitative analysis of glucose contained in an interstitial fluid, or the like.

The present invention also relates to a device for interstitial fluid extraction, which is used in an analyzing process of an interstitial fluid, comprising extracting the interstitial fluid in a hydrogel layer through the skin of a vertebrate subjected to a permeability-improving treatment, analyzing the interstitial fluid collected in the hydrogel layer after a predetermined period of time has elapsed to measure the concentrations of a sodium ion and glucose contained therein and calculating out a value corresponding to a glucose concentration in the blood of the vertebrate on the basis of these measured values, and an analyzing process of an interstitial fluid using the device for interstitial fluid extraction.

BACKGROUND ART

In mammal, blood glucose is a synonym of blood sugar. A serious diabetic is required to measure a blood glucose concentration generally 4 to 6 times per day. A general method for measuring the blood glucose concentration is a method of collecting a part of the blood of a patient and analyzing it. However, the analyzing method of frequently collecting the blood greatly burdens the patient and has a possibility that the patient may be infected with an infectious disease through the part where the blood has been collected. Therefore, there is proposed a method of extracting an interstitial fluid present under the skin of a patient through the skin and measuring a glucose concentration in the interstitial fluid collected.

In the present invention, "tissue" means a combination of cells gathered for fulfilling a particular role in vivo and intercellular cements filled therebetween. The tissue of a vertebrate such as human is generally roughly divided into 4 tissues of an epithelial tissue, a supporting tissue (for example, fibrous connective tissue, cartilaginous tissue, bone tissue, blood and lymph), a muscular tissue and a nervous tissue. "Interstitial fluid" generally means a fluid component (also referred to as "intercellular fluid") present between cells and becoming an environment of the cells in the tissue of a vertebrate such as human.

For example, WO 96/00110 (Patent Literature 1) proposes an ion-introducing device having a collecting reserver having ion conductive hydrogel, first and second ion-introducing electrodes, and a sensor coming into contact with the collecting reserver, and adapted for transferring glucose or a glucose metabolite to the collecting reserver by applying electric energy to percutaneously monitor a target substance. The ion conductive hydrogel of Patent Literature 1 is specifically a crosslinked acrylic acid polymer containing NaCl and $NaHCO_3$ for applying a high ion conductivity.

When a pad composed of the ion conductive hydrogel is struck on the skin of a subject to apply electric energy thereto, an interstitial fluid containing glucose is transferred to the pad through the skin, and the glucose then reacts with a glucose oxidase contained in the ion conductive hydrogel in the pad to generate hydrogen peroxide. A current proportional to the concentration of hydrogen peroxide in the pad is generated in a sensor operating electrode, and this current gives a signal interpreted by a system controller to display the concentration of glucose on a display. Patent Literature 1 describes that when the actual concentration of blood glucose of the subject is measured, that concentration can be correlated with the above-described glucose concentration.

WO 97/02811 (Patent Literature 2) proposes a hydrogel patch comprising a hydrophilic compound forming hydrogel in the presence of water, water in an amount of at most 95% by weight based on the weight of the hydrogel, an enzyme reacting with glucose and an electrolyte. This hydrogel patch is also adopted for measuring a glucose concentration by measuring a current generated by a reaction of the enzyme with glucose like the ion conductive hydrogel described in Patent Literature 1 and is such that transfer of glucose from a subject to the hydrogel patch is also conducted by an electroosmotic method.

Patent Literature 2 exemplifies polyethylene oxide, polyvinyl alcohol, polyacrylic acid, polyacrylamide methylpropanesulfonate and polyvinyl pyrrolidone as hydrophilic compounds forming hydrogel. The hydrogel of Patent Literature 2 contains a chloride ion-containing salt typified by NaCl as the electrolyte and a glucose oxidase as the enzyme.

When the ion-introducing device or the hydrogel patch disclosed in Patent Literature 1 or Patent Literature 2 is used, an interstitial fluid can be percutaneously extracted by the hydrogel struck on surface of the skin without collecting blood to determine the concentration of glucose contained in the interstitial fluid by analyzing the interstitial fluid collected in the hydrogel after a predetermined period of time has elapsed. When that concentration is correlated with a blood glucose concentration measured by collecting the blood, a value corresponding to the concentration of glucose in the blood can be obtained.

However, the ion-introducing device and the hydrogel patch disclosed in Patent Literatures 1 and 2 both contain a relatively large amount of a sodium ion in the hydrogel for imparting electric conductivity to the hydrogel and an enzyme for metabolizing glucose, such as a glucose oxidase.

When micropores are formed from the surface of the skin to a horny layer by applying electric energy like the technique described in Patent Literatures 1 and 2 for extracting the interstitial fluid using the hydrogel, the amount of glucose in the interstitial fluid collected in the hydrogel varies according to the hole diameter and depth of the micropores, a measured portion on the skin, and the like. Therefore, a value corresponding to the concentration of blood sugar glucose in the blood cannot be exactly obtained by the mere measurement of a glucose concentration in the interstitial fluid, so that in Patent Literature 1, a processing of correlating the measured glucose concentration with a blood glucose concentration measured by actually collecting the blood is conducted.

CITATION LIST

Patent Literature

Patent Literature 1: WO 96/00110
Patent Literature 2: WO 97/02811

SUMMARY OF INVENTION

Technical Problem

It is an object of the present invention to provide a device for interstitial fluid extraction equipped with a hydrogel layer, by which a value correlated with a blood glucose concentration can be determined from the concentration of glucose contained in an interstitial fluid collected without being correlated with a blood glucose concentration measured by actually collecting the blood.

More specifically, a main object of the present invention is to provide a device for interstitial fluid extraction, which can be used in an analyzing process of the interstitial fluid, comprising extracting the interstitial fluid in a hydrogel layer through the skin of a vertebrate subjected to a permeability-improving treatment, analyzing the interstitial fluid collected in the hydrogel layer to measure the concentrations of a sodium ion and glucose contained therein and calculating out a value corresponding to a glucose concentration in the blood of the vertebrate on the basis of these measured values.

Another object of the present invention is to provide a production process of the device for interstitial fluid extraction. A further object of the present invention is to provide an analyzing process of an interstitial fluid using the device for interstitial fluid extraction.

The present inventors have carried out an extensive investigation with a view toward achieving the above objects. As a result, the present inventors have reached a device for interstitial fluid extraction, in which a pressure sensitive adhesive layer is arranged on one surface of a base material formed from a synthetic resin film, a hydrogel layer formed from at least one hydrophilic polymer selected from the group consisting of polyvinyl alcohol and polyvinyl pyrrolidone is arranged on the surface of the pressure sensitive adhesive layer, and a release layer covering exposed surfaces of both pressure sensitive adhesive layer and hydrogel layer is provided.

A part of the pressure sensitive adhesive layer is exposed from around the hydrogel layer. The hydrogel layer does substantially not contain a sodium ion. The hydrogel layer causes no water separation when measured according to the measuring method (measuring method described in Examples) described in the present description. The hydrogel layer does substantially not contain an enzyme metabolizing an interstitial fluid component, such as a glucose oxidase.

The hydrogel layer in the device for interstitial fluid extraction according to the present invention is preferably that crosslinked by irradiation of radiation because mixing of various chemical substances attending on adoption of a chemical crosslinking method is prevented. The hydrogel layer is high in water content, but separation of water therefrom is not observed. This fact means that the crosslinking reaction in the hydrogel layer by irradiation of radiation sufficiently progresses without being inhibited.

The hydrogel layer preferably contains an osmotic pressure control agent for increasing an osmotic pressure to improve the interstitial fluid extraction efficiency thereof. On the other hand, an aqueous solution of a hydrophilic polymer containing the osmotic pressure control agent tends to inhibit the crosslinking reaction by irradiation of radiation. The present inventors have found that the concentrations of the hydrophilic polymer and the osmotic pressure control agent in the aqueous solution of the hydrophilic polymer are controlled in addition to the use of a specified compound as the osmotic pressure control agent, whereby the crosslinking reaction by irradiation of radiation sufficiently progresses to obtain a hydrogel layer causing no water separation.

The concentrations of a sodium ion and glucose in the interstitial fluid collected in the hydrogel layer can be exactly measured by means of a biocomponent analysis unit having a structure suitable for application of the device for interstitial fluid extraction and an analyzing function. The biocomponent analysis unit is used, whereby the concentrations of the sodium ion and glucose in the interstitial fluid can be exactly measured, and a value corresponding to a blood glucose concentration can be calculated out on the basis of these measured values to display it. The present invention has been led to completion on the basis of these findings.

Solution to Problem

According to the present invention, there is provided a device for interstitial fluid extraction, comprising
a base material formed from a synthetic resin film;
a pressure sensitive adhesive layer arranged on one surface of the base material;
a hydrogel layer arranged on the surface of the pressure sensitive adhesive layer and formed from at least one hydrophilic polymer selected from the group consisting of polyvinyl alcohol and polyvinyl pyrrolidone; and
a release layer covering exposed surfaces of both pressure sensitive adhesive layer and hydrogel layer, wherein
the hydrogel layer has an area of a size that the pressure sensitive adhesive layer is exposed from around the hydrogel layer, does substantially not contain a sodium ion and causes no water separation when measured according to the measuring method described in the present description.

According to the present invention, there is also provided a production process of a device for interstitial fluid extraction, comprising
providing a base material formed from a synthetic resin film;
arranging a pressure sensitive adhesive layer on one surface of the base material;
arranging a hydrogel layer formed by irradiating a coating film of an aqueous solution of at least one hydrophilic polymer selected from the group consisting of polyvinyl alcohol and polyvinyl pyrrolidone with radiation to crosslink the hydrophilic polymer on the surface of the pressure sensitive adhesive layer; and
covering exposed surfaces of both pressure sensitive adhesive layer and hydrogel layer with a release layer, wherein
the hydrogel layer has an area of a size that the pressure sensitive adhesive layer is exposed from around the hydrogel layer, does substantially not contain a sodium ion and causes no water separation when measured according to the measuring method described in the present description.

According to the present invention, there is further provided an analyzing process of an interstitial fluid, comprising extracting the interstitial fluid in a hydrogel layer through the skin of a vertebrate subjected to a permeability-improving treatment, analyzing the interstitial fluid collected in the hydrogel layer after a predetermined period of time has elapsed to measure the concentrations of a sodium ion and glucose contained therein and calculating out a value corresponding to a glucose concentration in the blood of the vertebrate on the basis of these measured values, wherein the above-described device for interstitial fluid extraction is used.

According to the present invention, there is still further provided a device for interstitial fluid extraction, by which an interstitial fluid is extracted in a hydrogel layer through the skin of a vertebrate subjected to a permeability-improving treatment on the basis of a difference in osmotic pressure, and which comprises
a base material formed from a synthetic resin film;
a pressure sensitive adhesive layer arranged on one surface of the base material;
a hydrogel layer arranged on the surface of the pressure sensitive adhesive layer and formed from at least one hydrophilic polymer selected from the group consisting of polyvinyl alcohol and polyvinyl pyrrolidone; and
a release layer covering exposed surfaces of both pressure sensitive adhesive layer and hydrogel layer, wherein
the hydrogel layer contains an osmotic pressure control agent, does substantially not contain a sodium ion, and satisfies, assuming that the concentration of the hydrophilic polymer is b % by weight, and the osmolarity of the osmotic pressure control agent is a osmole(s), the relationship represented by the following expression (A):

$$a \leq 0.1b - 0.6 \tag{A}$$

(however, $0.05 \leq a \leq 0.94$, and $7 \leq b \leq 30$).

Advantageous Effects of Invention

According to the present invention, there is provided a device for interstitial fluid extraction, which is easy to be applied to a skin surface, inhibits irritation to the skin and is equipped with a hydrogel layer of a hydrophilic polymer capable of exactly analyzing amounts of a sodium ion and glucose contained in the interstitial fluid collected.

In particular, the device for interstitial fluid extraction according to the present invention can be suitably used in an analyzing process of an interstitial fluid, comprising extracting the interstitial fluid in the hydrogel layer through the skin of a vertebrate, analyzing the interstitial fluid collected in the hydrogel layer after a predetermined period of time has elapsed to measure the concentrations of a sodium ion and glucose contained therein and calculating out a value corresponding to a glucose concentration in the blood of the vertebrate on the basis of these measured values.

According to the present invention, there are also provided a production process of the device for interstitial fluid extraction and an analyzing process of an interstitial fluid using the device for interstitial fluid extraction.

DESCRIPTION OF EMBODIMENTS

The device for interstitial fluid extraction according to the present invention is intended for an interstitial fluid extracted and collected through a skin tissue subjected to a permeability-improving treatment. The skin tissue includes a horny layer and a mucosal tissue. In many cases, however, the horny layer becomes an object The device for interstitial fluid extraction according to the present invention can be suitably applied to an analyzing process of an interstitial fluid, comprising extracting the interstitial fluid in the hydrogel layer through the skin of a vertebrate such as human, which has been subjected to a permeability-improving treatment, analyzing the interstitial fluid collected in the hydrogel layer to measure the concentrations of a sodium ion and glucose contained therein and calculating out a value corresponding to a glucose concentration in the blood of the vertebrate on the basis of these measured values.

With respect to the device for interstitial fluid extraction according to the present invention, the details thereof, including a biocomponent analysis unit suitable for the analyzing process, will hereinafter be described.

Figure 1:
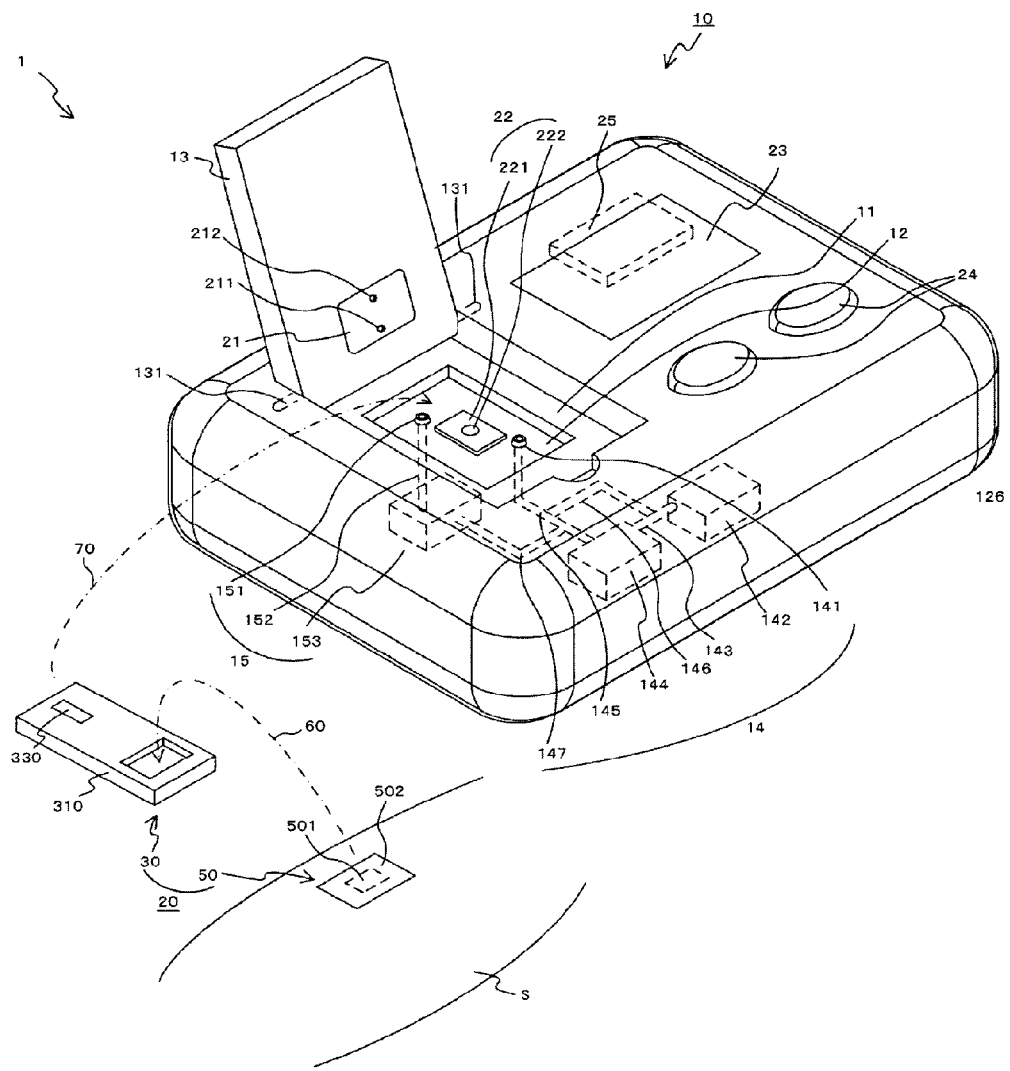
FIG. 1 is a perspective view illustrating the appearance of an exemplary biocomponent analysis unit which can be used for an analyzing process of an interstitial fluid according to the present invention.

FIG. 1 is a perspective view illustrating the appearance of an exemplary biocomponent analysis unit which can be used for the analyzing process of the interstitial fluid according to the present invention. The biocomponent analysis unit 1 is equipped with an analysis unit body 10 and an analyzing kit 20 as illustrated in FIG. 1. The analyzing kit 20 is equipped with a cartridge 30 for analysis and a device 50 for interstitial fluid extraction. This biocomponent analysis unit 1 is used for obtaining a value corresponding to a blood glucose concentration by extracting an interstitial fluid from a subject through the skin thereof by the device 50 for interstitial fluid extraction and analyzing concentrations of a sodium ion and glucose in the interstitial fluid collected in the device for interstitial fluid extraction after a predetermined period of time.

More specifically, this biocomponent analysis unit 1 is used in the following manner. First, micropores are formed in the skin of a subject as the permeability-improving treatment, and the device 50 for interstitial fluid extraction is then stuck on the surface of the skin subjected to the permeability-improving treatment. Accordingly, the permeability-improving treatment in the present invention typically means a treatment for forming micropores in the skin of a vertebrate such as human. The micropores in the skin having a horny layer are preferably formed through the horny layer from the viewpoint of improvement in permeability of an interstitial fluid. The device 50 for interstitial fluid extraction extracts the interstitial fluid in the hydrogel layer on the basis of a difference in osmotic pressure. Therefore, the device 50 for interstitial fluid extraction can extract the interstitial fluid in the hydrogel layer without applying any electric energy.

After a certain period of time has elapsed from the sticking of the device 50 for interstitial fluid extraction on the surface of the skin subjected to the permeability-imparting treatment, the device 50 for interstitial fluid extraction is taken out of the skin of the subject and stuck on the cartridge 30 for analysis as illustrated by a dashed line 60 in FIG. 1. The cartridge 30 for analysis is arranged in a cartridge arranging part 12 of the unit body 10 as illustrated by a dashed line 70. The unit body 10 executes a prescribed analytical processing for the device 50 for interstitial fluid extraction stuck on the cartridge 30 for analysis arranged in the cartridge arranging part 12 to measure concentrations of glucose and a sodium ion in the interstitial fluid collected in the device 50 for interstitial fluid extraction and calculate out a value corresponding to a blood glucose concentration on the basis of these measured values. When the extraction time of the device 50 for interstitial fluid extraction is set to at least 60 minutes, the concentrations of glucose and a sodium ion in the interstitial fluid collected can be measured to calculate out a value corresponding to a blood sugar AUC (area under the curve) value on the basis of these measured values.

The mechanism of the analysis unit body 10 will hereinafter be described. As illustrated in FIG. 1, the analysis unit body 10 is equipped with a thick rectangular housing as illustrated in FIG. 1, and a recessed part 11 is formed in a top plate on an upper surface of the housing. The cartridge arranging part 12 composed of a recessed part formed deeper than the recessed part 11 is provided in the recessed part 11. A movable top plate 13 having the same thickness as the height of a side wall of the recessed part 11 is joined to the recessed part 11.

The movable top plate 13 is joined to the side walls of the recessed part 11 by fitting a support shaft 131 extending horizontally from the side walls thereof into the side walls of the recessed part 11. The movable top plate 13 can be received in the recessed part 11 from the state illustrated in FIG. 1 by being moved around the support shaft 131 and to the contrary, raised as illustrated in FIG. 1 from the state received in the recessed part 11. The cartridge arranging part 12 has a size capable of receiving the cartridge 30 for analysis therein.

The movable top plate 13 is supported by the support shaft so as to be biased toward the recessed part 11. Accordingly, the cartridge 30 for analysis arranged in the cartridge arranging part 12 is pressed from above by the movable top plate 13. An injection nipple 141 and a discharge nipple 151 provided so as to project from a bottom surface of the cartridge arranging part 12 also functions as cushioning members when pressed by the movable top plate 13 because they are made by a member having flexibility. The movable top plate 13 presses the cartridge 30 for analysis from above, whereby close contact of the respective nipples with an inlet hole and an outlet hole formed in the cartridge 30 for analysis becomes firmer to reduce the risk of liquid leakage.

The analysis unit body 10 is equipped with a liquid supply part 14 and a liquid discharge part 15 in its interior. The liquid supply part 14 is a mechanism for supplying a liquid to the cartridge 30 for analysis arranged in the cartridge arranging part 12. The liquid discharge part 15 is a mechanism for discharging the liquid supplied to the cartridge 30 for analysis as a waste liquid.

Figure 2:
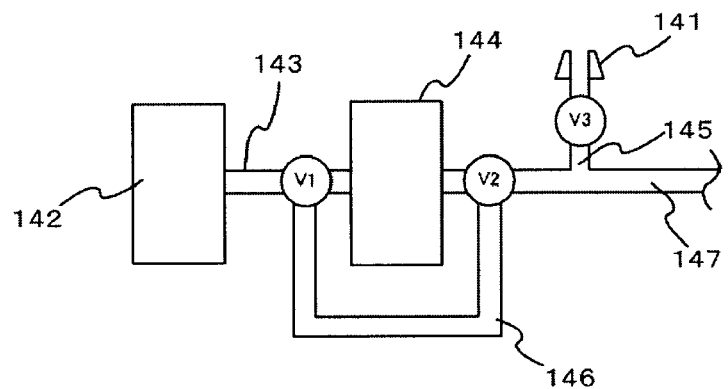
FIG. 2 typically illustrates the construction of a liquid supply part 14 in the biocomponent analysis unit in FIG. 1.

FIG. 2 typically illustrates the construction of the liquid supply part 14. As illustrated in FIG. 2, the liquid supply part 14 is equipped with an injection nipple 141, a pump 142 and a recovery liquid tank 144. The pump 142 and recovery liquid tank 144 are connected to each other by an upstream-side passage 143. The recovery liquid tank 144 and injection nipple 141 are connected to each other by a downstream-side passage 145. The pump 142 and injection nipple 141 are connected to each other by a bypass passage 146 bypassing the recovery liquid tank 144.

An electromagnetic valve V1 is provided at a junction of the upstream-side passage 143 with the bypass passage 146. An electromagnetic valve V2 is provided at a junction of the downstream-side passage 145 with the bypass passage 146. An electromagnetic valve V3 is provided on a downstream side from the junction of the downstream-side passage 145 with the bypass passage 146. A passage between the electromagnetic valves V2 and V3 is linked to a waste liquid passage 147 linking to a waste liquid tank 153 of the liquid discharge part 15.

The injection nipple 141 is provided at the cartridge arranging part 12 so as to protrude upward and supports the cartridge 30 for analysis from below together with the discharge nipple 151 when the cartridge 30 for analysis has been arranged in the cartridge arranging part 12. A liquid is injected in the interior of the cartridge 30 for analysis arranged in the cartridge arranging part 12 through the injection nipple 141.

The injection nipple 141 is made by a flexible member such as rubber. The discharge nipple 151 is also made by the flexible member likewise, whereby the injection nipple 141 and discharge nipple 151 can be brought into tight contact with the inlet hole and outlet hole formed in the cartridge 30 for analysis, respectively, when the cartridge 30 for analysis has been arranged in the cartridge arranging part 12, which makes hard to cause liquid leakage. The pump 142 is driven by a motor to send air within the passage.

The recovery liquid tank 144 stores a recovery liquid (recovery liquid for recovering a biocomponent from the interstitial fluid collected in the hydrogel layer) injected in the interior of the cartridge 30 for analysis. If impurities are contained in the recovery liquid, the impurities affect the detection of glucose and the sodium ion. Therefore, the recovery liquid is preferably a liquid substantially containing no impurity. From such a viewpoint, it is desirable that pure water is stored as the recovery liquid in the recovery liquid tank 144. The recovery liquid tank 144 is constructed removably out of the unit body 10. The supplement of the recovery liquid is conducted by replacing the recovery tank 144 with new one.

The electromagnetic valve V1 changes over the connection between the upstream-side passage 143 and the recovery liquid tank 144 to the connection between the upstream-side passage 143 and the bypass passage 146 by opening and closing the valve. The electromagnetic valve V2 changes over the connection between the recovery liquid tank 144 and the downstream-side passage 145 to the connection between the bypass passage 146 and the downstream-side passage 145 by opening and closing the valve. The electromagnetic valve V3 changes over the opening and closing of the downstream-side passage 145 by opening and closing the valve.

The liquid supply part 14 is equipped with the above-described construction, whereby only a predetermined amount of the recovery liquid stored in the recovery liquid tank 144 can be sent to the cartridge 30 for analysis by sending air from the pump 142.

Figure 3:
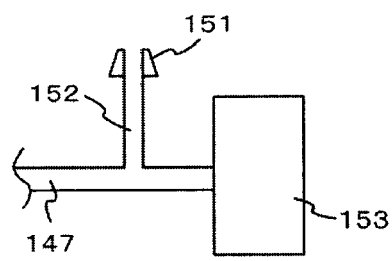
FIG. 3 typically illustrates the construction of a liquid discharge part 15 in the biocomponent analysis unit in FIG. 1.

FIG. 3 typically illustrates the construction of a liquid discharge part 15. The liquid discharge part 15 is equipped with a discharge nipple 151, a passage 152 and a waste liquid tank 153. The discharge nipple 151 is provided at the cartridge arranging part 12 so as to protrude upward and supports the cartridge 30 for analysis from below together with the injection nipple 141 when the cartridge 30 for analysis has been arranged in the cartridge arranging part 12. The recovery liquid sent from the liquid supply part 14 is taken in the cartridge 30 for analysis through the injection nipple 141.

The waste liquid tank 153 is connected to the discharge nipple 151 through the passage 152 and stores a waste liquid of the recovery liquid taken in from the discharge nipple 151. The waste liquid tank 153 is constructed connectably to the outside of the unit body 10 so as to enable the waste liquid to be discharged to the outside of the unit body 10.

As illustrated in FIG. 1, the unit body 10 is equipped with a glucose detection part 21, a sodium detection part 22, a display part 23, an operation part 24 and a control part 25. The glucose detection part 21 is provided at a back surface (i.e., a surface facing the cartridge arranging part 12 when the movable top plate 13 is received in the recessed part 11) of the movable top plate 13.

The glucose detection part 21 is equipped with a light source 211 for irradiating with light and a light reception part 212 for receiving reflected light of the light irradiated from the light source 211, whereby the glucose detection part 21 is so constructed that the cartridge 30 for analysis arranged in the cartridge arranging part 12 can be irradiated with the light, and the reflected light from the cartridge 30 for analysis irradiated can be received. The cartridge 30 for analysis contains reaction reagents (reactive substances) 330 such as a glucose oxidase and a pigment reacting with an active oxygen of hydrogen peroxide formed by the oxidase to develop a color. The glucose detection part 21 detects a change in absorbance by such a chemical reaction of glucose and the reagents by the reflected light, thereby quantitatively analyzing glucose.

The sodium detection part 22 is provided at the bottom surface of the cartridge arranging part 12. The sodium detection part 22 is equipped with a rectangular plate-like member 221 provided at the bottom surface of the cartridge arranging part 12, and a pair of electrodes 222 for measurement of a sodium ion concentration is provided at the substantial center of this plate-like member 221. The electrodes 222 for measurement of the sodium ion concentration include a sodium ion-selective electrode equipped with a sodium ion selecting membrane and composed of silver/silver chloride and a silver/silver chloride electrode that is a counter electrode.

Figure 6:
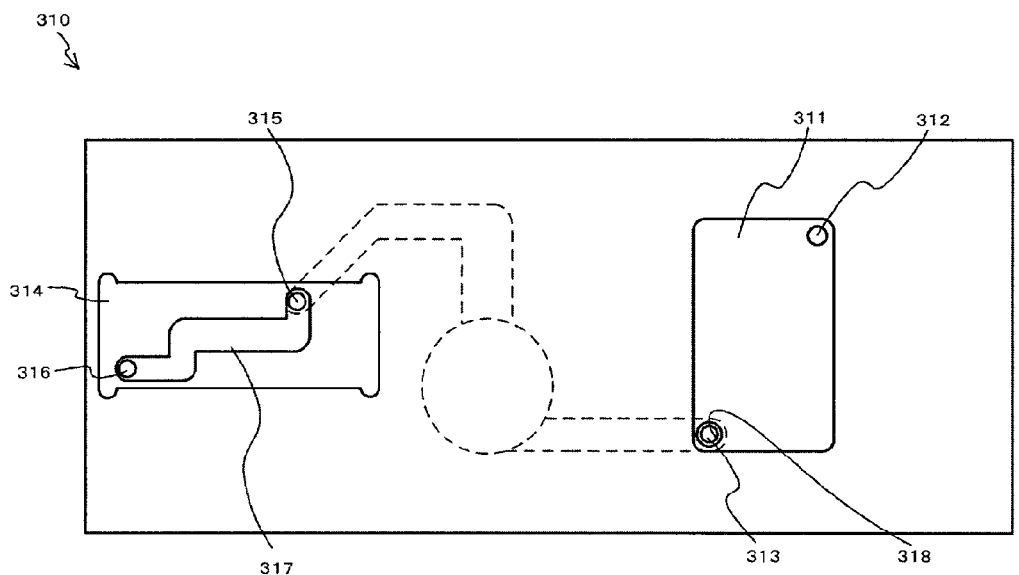
FIG. 6 is a plan view of a cartridge body 310 for analysis.
Figure 7:
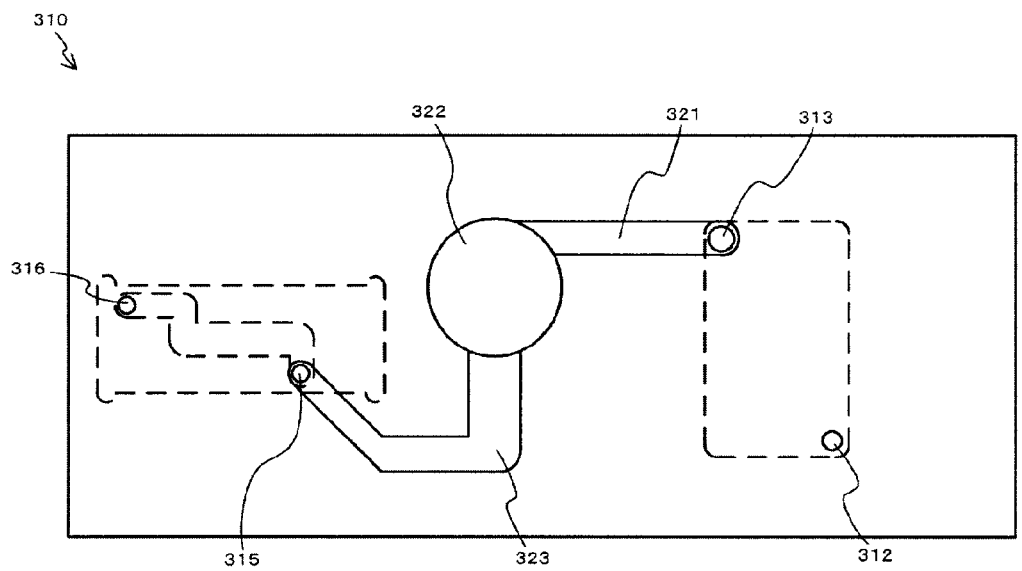
FIG. 7 is another plan view of the cartridge body 310 for analysis.

The plate-like member 221 is covered with a flexible material and also functions as a cushioning member when the cartridge 30 for analysis arranged in the cartridge arranging part 12 is pressed by the movable top plate 13. The plate-like member 221 forms a closed space with a recessed part (a first connection passage, a storage part for sodium detection, and a second connection passage; see FIGS. 6 and 7 illustrated below) formed in a lower surface of the cartridge 30 for analysis, and this space functions as a passage through which the liquid passes. From the viewpoint of preventing liquid leakage, thus the cartridge 30 for analysis and the plate-like member 221 preferably comes into tight contact with each other. In a preferred embodiment, the construction that the surface of the plate-like member 221 is covered with a flexible material, and the cartridge 30 for analysis is pressed from above by the movable top plate 13 can improve the close contact between the plate-like member 221 and the cartridge 30 for analysis.

The display part 23 illustrated in FIG. 1 is provided on an upper surface of the housing of the unit body 10 and constructed comprising a liquid crystal panel. This display part 23 functions in such a manner that an operation image is displayed for a user upon operation, and a measured result is displayed at the time the measurement has been completed.

The operation part 24 illustrated in FIG. 1 is provided on the upper surface of the housing of the unit body 10 and constructed comprising a plurality of buttons. A user can direct beginning and shut-down of measurement to the control part 25 by operating these.

The control part 25 illustrated in FIG. 1 is provided in the interior of the unit body 10 and equipped with a control mechanism composed of CPU, ROM, RAM and the like. CPU reads and executes a program stored in ROM, thereby controlling the operations of the respective parts. RAM is used as a developing region of the program when the program stored in ROM is executed.

As illustrated in FIG. 1, the analyzing kit 20 is composed of the cartridge 30 for analysis and the device 50 for interstitial fluid extraction stuck on the cartridge 30 for analysis. The analyzing kit 20 is provided separately with the cartridge 30 for analysis and the device 50 for interstitial fluid extraction before it is used in the analysis. Upon using in the analysis, the device 50 for interstitial fluid extraction is stuck on the cartridge 30 for analysis.

Figure 4:
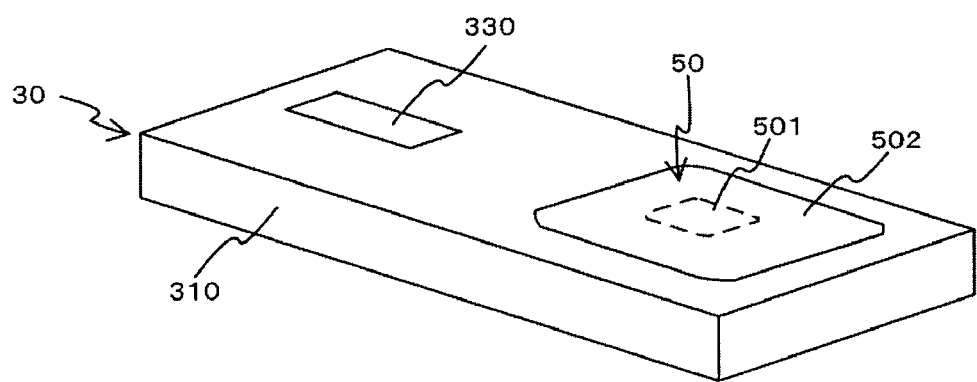
FIG. 4 is a perspective view illustrating a state that a device 50 for interstitial fluid extraction has been stuck on a cartridge 30 for analysis in the biocomponent analysis unit in FIG. 1.

FIG. 4 is a perspective view illustrating a state that the device 50 for interstitial fluid extraction has been stuck on the cartridge 30 for analysis. As illustrated in FIG. 4, the cartridge 30 for analysis is mainly equipped with a cartridge body 310 and the reaction reagents 330 to glucose. FIG. 4 illustrates the cartridge body 310 with its detailed structure omitted.

Figure 5A:
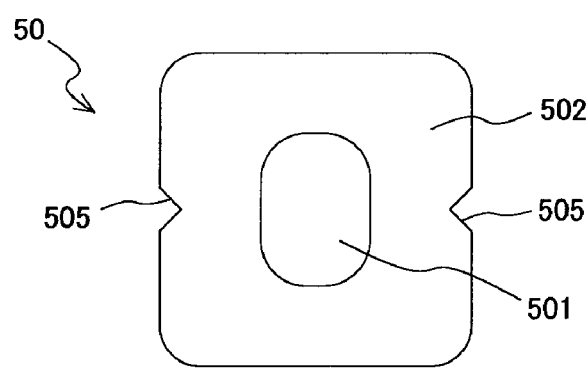
FIG. 5a is a plan view illustrating the structure of a device for interstitial fluid extraction.

The device 50 for interstitial fluid extraction is described with reference to FIGS. 5a and 5b. FIG. 5a is a plan view illustrating the structure of the device 50 for interstitial fluid extraction. In FIG. 5a, a lower surface (a surface coming into contact with the skin in FIG. 1) of the device 50 for interstitial fluid extraction is illustrated in an exposed state. In the following description, a surface of the device 50 for interstitial fluid extraction, with which the skin comes into contact, is referred to as a lower surface, and a back surface (opposing surface) thereof is referred to as an upper surface.

The device 50 for interstitial fluid extraction is equipped with the hydrogel layer 501 and a pressure sensitive adhesive film 502 and has a structure that the hydrogel layer 501 is held on the substantial center of the pressure sensitive adhesive film 502. The pressure sensitive adhesive film 502 is composed of a base material and a pressure sensitive adhesive layer.

The device for interstitial fluid extraction according to the present invention has a multilayer structure that
a) a base material formed from a synthetic resin film,
b) a pressure sensitive adhesive layer,
c) a hydrogel layer formed from a hydrophilic polymer, and
d) a release layer
are arranged in this order.

When the pressure sensitive adhesive layer is formed from a pressure sensitive adhesive comprising a hydrophobic polymer as a base, adhesion between the pressure sensitive adhesive layer and the hydrogel layer formed from the hydrophilic polymer may be insufficient in some cases. In such a case, an intermediate layer formed of a material having good adhesion to both layers may be arranged between the pressure sensitive adhesive layer and the hydrogel layer.

In general, the base material is desirably a synthetic resin film having flexibility and good resistance to moisture permeation. In the device for interstitial fluid extraction according to the present invention, the hydrogel layer has a function of extracting an interstitial fluid through the skin and collecting the interstitial fluid extracted over a predetermined period of time. Therefore, the base material present on the side opposing to the hydrogel layer is required to have sufficient resistance to moisture permeation not to vaporize off water in the hydrogel layer and an interstitial fluid component collected. The base material is also required to have cushioning property and protective property for a skin site on which the device for interstitial fluid extraction is stuck.

From these points in view, as the synthetic resin film forming the base material, is preferred, for example, a polyethylene film, a polypropylene film, a polyester film or a polyurethane film, and more preferred a polyethylene film, a polyester film or a polyurethane film. The thickness of the synthetic resin film is within a range of preferably from 30 to 250 μm, more preferably from 40 to 200 μm, particularly preferably from 50 to 120 μm.

Examples of the pressure sensitive adhesive forming the pressure sensitive adhesive layer include acrylic pressure sensitive adhesives, rubber-based pressure sensitive adhesives, silicone-based pressure sensitive adhesives and urethane-based pressure sensitive adhesives. Since the device for interstitial fluid extraction according to the present invention is often stuck on a skin surface over a relatively long period of time, these pressure sensitive adhesives are preferably little in skin irritativity. Acrylic pressure sensitive adhesives and rubber-based pressure sensitive adhesives are preferred from the viewpoint of little skin irritativity, and acrylic pressure sensitive adhesives are more preferred.

The acrylic pressure sensitive adhesive used in the present invention is an alkyl (meth)acrylate copolymer comprising, as a main component, an alkyl acrylate or alkyl methacrylate having 1 to 18 carbon atoms, preferably 4 to 12 carbon atoms. Here, the alkyl (meth)acrylate means an alkyl acrylate or alkyl (meth)acrylate.

Examples of the alkyl (meth)acrylate include methyl (meth)acrylate, ethyl (meth)acrylate, n-butyl (meth)acrylate, isobutyl (meth)acrylate, t-butyl (meth)acrylate, n-hexyl (meth)acrylate, n-octyl (meth)acrylate, 2-ethylhexyl (meth) acrylate, isooctyl (meth)acrylate, isononyl (meth)acrylate, n-decyl (meth)acrylate, isodecyl (meth)acrylate, lauryl (meth)acrylate and stearyl (meth)acrylate.

These alkyl (meth)acrylates may be used either singly or in combination of 2 or more monomers thereof. Among the alkyl (meth)acrylates, n-butyl (meth)acrylate, 2-ethylhexyl (meth)acrylate, n-octyl (meth)acrylate, isooctyl (meth)acrylate and isononyl (meth)acrylate are preferred.

The alkyl (meth)acrylate copolymer is a copolymer comprising, as a main monomer component, an alkyl (meth) acrylate, whereby the copolymer can exhibit properties as the acrylic pressure sensitive adhesive. The copolymerization proportion of the alkyl (meth)acrylate is preferably 60 to 90% by weight, more preferably 65 to 97% by weight, particularly preferably 70 to 96% by weight.

As a comonomer copolymerizing with the alkyl (meth) acrylate, is preferred a vinyl monomer having a functional group. Specific examples thereof include acrylates having a hydroxyl group, such as 2-hydroxyethyl acrylate, 3-hydroxypropyl acrylate and 4-hydroxybutyl acrylate; vinyl monomers having a carboxyl group, such as acrylic acid, methacrylic acid, maleic acid, maleic anhydride, itaconic acid and monobutyl maleate; vinyl monomers having an amide group, such as acrylamide, dimethylacrylamide, diethylacrylamide, methacrylamide and N-methylolacrylamide; vinyl monomers having an amino group, such as dimethylaminoethyl acrylate; vinyl monomers having an epoxy group, such as glycidyl acrylate and glycidyl methacrylate; vinyl monomers having a pyrrolidone ring, such as N-vinylpyrrolidone; and alkoxyalkyl acrylates such as 2-methoxyethyl acrylate and ethoxyethyl acrylate. The monomers having the functional group may be used either singly or in combination of 2 or more monomers thereof. The copolymerization proportion of the monomer having the functional group in the alkyl (meth) acrylate copolymer is preferably 1 to 40% by weight, more preferably 2 to 35% by weight, particularly preferably 3 to 30% by weight.

Examples of other comonomers include vinyl esters such as vinyl acetate; unsaturated nitriles such as acrylonitrile and methacrylonitrile; and vinyl aromatic compounds such as styrene. The other comonomers may be used either singly or in combination of 2 or more monomers thereof. The copolymerization proportion of the other comonomer in the alkyl (meth)acrylate copolymer is preferably 0 to 30% by weight.

The alkyl (meth)acrylate copolymer can be generally synthesized by radical-polymerizing the monomers. Examples of a polymerization process include a solution polymerization process, an emulsion polymerization process and a bulk polymerization process. However, the solution polymerization process is preferred in that good tackiness is easily achieved. Examples of a polymerization initiator include organic peroxides such as benzoyl peroxide and lauroyl peroxide; and azo initiators such as azobisisobutyronitrile. The radical polymerization initiator is added in a proportion of about 0.1 to 3% by weight based on all the monomers, and the resultant mixture is stirred for from several hours to several tens hours at a temperature of about 40 to 90° C. under a nitrogen atmosphere to conduct copolymerization. In the solution polymerization process, ethyl acetate, acetone, toluene, or a mixture thereof is commonly used as a solvent.

The weight average molecular weight of the acrylic pressure sensitive adhesive is preferably 300,000 to 1,000,000, more preferably 450,000 to 650,000. The weight average molecular weight of the acrylic pressure sensitive adhesive is controlled within the above range, whereby cohesiveness, adhesive strength, workability upon mixing with other components, affinity for other components, and the like can be balanced with one another. The weight average molecular weight of the acrylic pressure sensitive adhesive is a value determined in terms of a value of standard polystyrene by gel permeation chromatography (GPC).

Various kinds of crosslinking agents may be used for increasing the cohesive strength of the acrylic pressure sensitive adhesive. Examples of the crosslinking agents include polyfunctional isocyanate compounds, polyfunctional epoxy compounds and polyvalent metal salts. When the crosslinking agent is added to the acrylic pressure sensitive adhesive, the used proportion thereof is preferably 0.01 to 3 parts by weight, more preferably 0.02 to 2 parts by weight, particularly preferably 0.03 to 1 part by weight per 100 parts by weight of the acrylic pressure sensitive adhesive. If the proportion of the crosslinking agent used is too low, the effect to increase the cohesive strength becomes little. If the proportion is too high, the cohesive strength is too increased.

Examples of the rubber-based pressure sensitive adhesive used in the present invention include compositions obtained by incorporating a tackifying resin, a softner and the like into a rubber base such as synthetic polyisoprene rubber, polyisobutylene, styrene-isoprene-styrene block copolymer (SIS), styrene-butadiene-styrene block copolymer (SBS) or styrene-ethylene.butylene-styrene block copolymer (SEBS). These rubber bases may be used either singly or in combination of 2 or more bases thereof. Among these rubber bases, thermoplastic elastomers such as SIS, SBS and SEBS are preferred in that sensitization to the skin is little, and crosslinking points are present in their molecules, with SIS being particularly preferred.

A tackifier is generally incorporated into the rubber-based pressure sensitive adhesive for increasing adhesive strength. As examples of the tackifier, may be mentioned C5 petroleum resins, C9 petroleum resins, terpene resins, rosin resins, phenol resins and xylene resins. The tackifier is used in a proportion of generally 50 to 350 parts by weight, preferably 80 to 300 parts by weight, more preferably 100 to 250 parts by weight per 100 parts by weight of the rubber base. The rubber-based pressure sensitive adhesive may contain a softner such as liquid paraffin, a filler, an antioxidant, a crosslinking agent, etc. as needed.

The coating of the pressure sensitive adhesive can be conducted by a method of coating a base material layer (synthetic resin film) with a pressure sensitive adhesive solution comprising an organic solvent or water as a medium by means of a coating device such as a reverse-roll coater, comma roll coater or bar coater. The pressure sensitive adhesive solution may be applied on to a paper base such as woodfree paper or glassine paper treated with a release agent such as a silicone resin, or a sheet such as a polyester film and dried to form a pressure sensitive adhesive layer, and a base material layer (synthetic resin film) may be then laminated on the pressure sensitive adhesive layer to transfer the pressure sensitive adhesive layer to one surface of the base material layer.

When the rubber-based pressure sensitive adhesive is used, the rubber-based pressure sensitive adhesive is heated and kneaded to melt it, and the melt is applied on to the base material layer (synthetic resin film). A method of applying the melt on to release paper and laminating the base material layer (synthetic resin film) on the resultant coating may also be adopted. Upon the coating, an organic solvent may be used, as needed, to apply a solution containing the rubber-based pressure sensitive adhesive.

In this manner, the pressure sensitive adhesive layer is arranged on one surface of the base material formed from the synthetic resin film. The thickness of the pressure sensitive adhesive layer is generally 10 to 250 µm, preferably 15 to 200 µm, more preferably 20 to 150 µm.

In the present description, a multilayer film having a layer structure of "synthetic resin film/pressure sensitive adhesive layer" may be called "pressure sensitive adhesive film" merely. One surface of the pressure sensitive adhesive film has pressure sensitive adhesion property because it is a pressure sensitive adhesive layer, and the other surface does not have the pressure sensitive adhesion property because it is a synthetic resin film. As illustrated in FIG. 5b, the pressure sensitive adhesive film 502 has a 2-layer structure of the base material layer 502a composed of the synthetic resin film and the pressure sensitive adhesive layer 502b.

The device for interstitial fluid extraction according to the present invention does desirably not vaporize off water from the hydrogel layer during sticking on the surface of the skin, to say nothing of during its storage. Therefore, the area of the pressure sensitive adhesive film (base material/pressure sensitive adhesive layer) is preferably larger by 1.2 to 30 times, more preferably 1.2 to 20 times, particularly preferably 1.5 to 15 times than the area (area stuck on the pressure sensitive adhesive layer) of the hydrogel layer. As described above, the area of the hydrogel layer is smaller than the area of the pressure sensitive adhesive layer (accordingly, base material/pressure sensitive adhesive layer), and the pressure sensitive adhesive layer is exposed from around the hydrogel layer. The device for interstitial fluid extraction can be brought into strong contact with the surface of the skin by the exposed surface of the pressure sensitive adhesive layer to fix it thereto.

Notches are preferably formed in the pressure sensitive adhesive film (base material/pressure sensitive adhesive layer) so as to become marks upon close contact of the device for interstitial fluid extraction with the surface of the skin. The notches are formed by triangular or semi-circular cutouts or projections to make positioning easy. FIG. 5a illustrates a case where notches each composed of a triangular cutout were formed in both sides of the pressure sensitive adhesive film.

A lead part may be formed at an end of the pressure sensitive adhesive film (base material/pressure sensitive adhesive layer). Since the device for interstitial fluid extraction according to the present invention is generally relatively small, the lead part is desirably provided for improving visibility and making the release layer easy to be peeled. The lead part is formed as a projected piece at the base material. However, the lead part may be formed by a method, in which no pressure sensitive adhesive layer is formed at that portion, or a method, in which a film or pressure sensitive adhesive film is additionally arranged on the pressure sensitive adhesive layer of that portion to make that portion noncohesive.

The lead part is preferably larger because ease of peeling from the release layer is improved. However, if the lead part is too large, sealing performance between the pressure sensitive adhesive film and the release layer is lowered, which forms the cause that water in the hydrogel layer held between them is vaporized off. Therefore, the area of the lead part is desirably controlled to at most 30% of the area of the pressure sensitive adhesive film. For example, when a pressure sensitive adhesive film (base material/pressure sensitive adhesive layer) 30 mm long and 30 mm wide is used, the width of the lead part is preferably controlled within a range of from 2 to 5 mm, preferably from 3 to 4 mm from the end of the pressure sensitive adhesive film. The lead part may be provided as one piece or two or more pieces, or around the whole periphery of the pressure sensitive adhesive film. The lead part may also be colored into various color tones such as blue.

The intermediate layer arranged between the pressure sensitive adhesive layer and the hydrogel layer is an optional layer and may be provided if necessary. The intermediate layer is a layer for improving the adhesion between the pressure sensitive adhesive layer and the hydrogel layer to integrate them. In particular, when a pressure sensitive adhesive layer formed of a hydrophobic pressure sensitive adhesive, for example, an acrylic pressure sensitive adhesive is arranged on one surface of the base material layer, the intermediate layer is interposed, whereby the hydrophobic pressure sensitive adhesive layer and the hydrophilic hydrogel layer can be brought into firm and close contact with each other. As a material used in the intermediate layer, may be mentioned various kinds of nonwoven fabrics or films. As the intermediate layer, is preferred a laminated product of a nonwoven fabric of polyethylene terephthalate (PET) and a PET film, or a polyethylene film from the viewpoints of good conformability to the hydrogel layer and transparency. The polyethylene film is also preferred from the viewpoint of flexibility. The area (area coming into contact with the pressure sensitive adhesive layer) of the intermediate layer is preferably almost equal to the area of the hydrogel layer.

The hydrogel layer is arranged directly or through the intermediate layer on the surface of the pressure sensitive adhesive layer. The hydrogel layer is a hydrogel layer formed from at least one hydrophilic polymer selected from the group consisting of polyvinyl alcohol (hereinafter may be abbreviated as "PVA") and polyvinyl pyrrolidone (hereinafter may be abbreviated as "PVP"). The hydrophilic polymer forming the hydrogel layer may be PVA alone or PVP alone or may be a mixture of both polymers. The hydrophilic polymer is preferably PVA alone or a mixture of PVA and PVP.

Hydrogel layer can be formed by a method of crosslinking the hydrophilic polymer in an aqueous solution thereof. The hydrogel layer can be formed by a method, in which an aqueous solution of the hydrophilic polymer is applied on to a base to form a coating film, and the hydrophilic polymer contained in the coating film is crosslinked. Crosslinking methods of the hydrophilic polymer include a chemical crosslinking method and a radiation-induced crosslinking method, and the radiation-induced crosslinking method is desirably adopted in that various chemical materials are hard to be mixed as impurities in the hydrogel layer.

The hydrogel layer arranged in the device for interstitial fluid extraction according to the present invention does substantially not contain a sodium ion and causes no water separation. The hydrogel layer has a function of extracting and collecting an interstitial fluid through the skin, and this function can be improved by increasing the osmotic pressure thereof. Therefore, it is desirable to contain an osmotic pressure control agent in the aqueous solution of the hydrophilic polymer upon preparation of the hydrogel layer. An electrolyte such as sodium chloride (NaCl) has heretofore been used for imparting electric conductivity to the hydrogel layer, but also acts as an osmotic pressure control agent.

However, when a hydrogel layer containing NaCl is used, it is difficult to exactly determine a minute amount of a sodium ion in an interstitial fluid extracted and collected through the skin. In order to extract the interstitial fluid by the hydrogel layer, it is necessary to form micropores from the surface of the skin to a horny layer. The glucose concentration in the interstitial fluid extracted by the hydrogel layer and collected in the hydrogel layer varies according to the hole diameter, number and depth of the micropores, a measured portion on the skin, and the like. The hydrogel layer substantially containing no sodium ion is used, whereby the condition of the micropores formed in the skin for extracting the interstitial fluid can be exactly monitored, and the minute amount of the sodium ion in the interstitial fluid collected can be exactly determined. In addition, the concentrations of the sodium ion and glucose in the interstitial fluid can be measured to exactly measure values corresponding to a blood glucose concentration and a blood sugar AUC value on the basis of these measured values.

Therefore, it is preferred that a sodium ion is substantially not caused to exist in the hydrogel layer. The allowable content of the sodium ion in the hydrogel layer of the present invention is at most 30 ppm, preferably at most 20 ppm, more preferably at most 10 ppm based on the weight from the viewpoint of reducing an error upon determination of a blood glucose concentration from the measured value of the glucose concentration using the measured value of the sodium ion concentration described above to at most 5%. The lower limit of the content of the sodium ion in the hydrogel layer of the present invention is zero (critical value of measurement). In the present invention, to substantially contain no sodium ion typically means that the sodium ion concentration in the hydrogel layer is at most 30 ppm based on the weight.

It is preferred that a compound (unsugar), which does substantially not contain a sodium ion and is non-analogous to glucose that is an object of analysis, is caused to be contained as an osmotic pressure control agent in the hydrogel layer from the viewpoint of improving the interstitial fluid extraction efficiency. From the viewpoint of the safety to the living body, as such an osmotic pressure control agent, may be used, for example, an inorganic osmotic pressure control agent such as ammonia, potassium chloride, potassium phosphate, magnesium chloride, magnesium phosphate, calcium chloride or calcium phosphate; an amino acid (organic osmotic pressure control agent) such as alanine, arginine, asparagine, aspargic acid, cysteine, glutamine, glutamic acid, glycine, histidine, isoleucine, leucine, lycine, methionine, phenylalanine, proline, serine, threonine, tryptophan, tyrosine or valine; a water-soluble vitamin (organic osmotic pressure control agent) such as thiamine, riboflavin, nicotinic acid amide, pyridoxine, cyanocobalamine or ascorbic acid; or a further organic osmotic pressure control agent such as tricine, urea or acetic acid. Among these osmotic pressure control agents, at least one compound selected from the group consisting of potassium chloride, potassium phosphate, magnesium chloride, magnesium phosphate, calcium chloride, calcium phosphate, amino acids, urea, acetic acid, ammonia, tricine, thiamine, riboflavin, nicotinic acid amide, pyridoxine, cyanocobalamine and ascorbic acid is preferred, and potassium chloride, urea, glycine, alanine and proline are particularly preferred.

These compounds are contained in the aqueous solution of the hydrophilic polymer prior to crosslinking. On the other hand, when these compounds are contained in the aqueous solution of the hydrophilic polymer prior to crosslinking, a crosslinking reaction by irradiation of radiation tends to be inhibited. Therefore, such an osmotic pressure control agent is preferably contained in the aqueous solution of the hydrophilic polymer in a proportion that the osmolarity thereof falls within a range of from 0.05 to 0.94 osmoles.

The degree of the osmotic pressure does not depend on the size and nature of a substance making up a solute and depends on only the number of particles. Such physical nature is called colligative property. An osmole (Osm) is used as an index indicating a concentration of a solute paying attention to this colligative property. The osmole is a unit of osmolarity and is equal to an osmolarity of a solution equal in osmotic pressure to an ideal solution of a nondissociative substance, which has a concentration of 1 mole in solute/1 litter (L) in solvent.

An actual osmolarity can be determined on the basis of the sum of concentrations of respective molecules contained in a solution. Therefore, the osmolarity [mole/L=osmole (Osm)] can be calculated out on the basis of the concentration (% by weight) of an osmotic pressure control agent such as potassium chloride (KCl). In, for example, 10 mM (millimol) of KCl, KCl is dissociated into a potassium ion and a chloride ion in an aqueous solution thereof, so that the number of particles becomes twice, and so the osmolarity thereof is 20 milliosmoles. When 10 mM of dissociative KCl and 5 mM of nondissociative urea are used in combination, the osmolarity is 25 milliosmoles (10×2+5).

The osmolarity of the osmotic pressure control agent is within a range of preferably from 0.05 to 0.94 osmoles, more preferably from 0.10 to 0.90 osmoles, particularly preferably from 0.20 to 0.80 osmoles. If the osmolarity of the osmotic pressure control agent is too low, the interstitial fluid extraction efficiency of the hydrogel layer is lowered. If the osmolarity is too high, the crosslinking reaction of the aqueous solution of the hydrophilic polymer by irradiation of radiation tends to be inhibited. However, the extracting function of the device for interstitial fluid extraction can be developed by controlling the size of the hydrogel layer, a time stuck on the skin surface, etc. without using any osmotic pressure control agent.

The hydrogel layer 501 illustrated in FIG. 5a is mainly intended to continuously extract an interstitial fluid through micropores formed in the horny layer by the permeability-improving treatment to obtain a value corresponding to a blood sugar AUC value. The glucose concentration is greatly affected by not only a blood sugar value, but also the size and depth of the micropores formed. As described above, the amount of the interstitial fluid collected varies according to the condition of the micropores provided in the horny layer, so that the mere measurement of the glucose content in the interstitial fluid collected cannot exactly calculate out the blood glucose concentration and blood sugar AUC value. In order to solve this problem, it is effective to normalize the amount of the interstitial fluid collected by collecting a sodium ion at the same time as glucose to measure the amount of the sodium ion. Therefore, the hydrogel layer 501 is desirably one substantially containing no sodium ion.

In order to conduct the measurement with high precision, glucose in an amount more than a measurable lower limit of a glucose measuring sensor must be collected. When a osmotic pressure control agent such as KCl is added into the hydrogel layer 501, the osmotic pressure of the hydrogel layer 501 becomes higher than the osmotic pressure of an interstitial fluid of a living body, and the interstitial fluid extraction efficiency becomes high. Therefore, it is desirable to contain the osmotic pressure control agent such as KCl in the hydrogel layer. Quite naturally, a hydrogel layer sufficiently containing water and substantially containing no sodium ion can extract an interstitial fluid containing glucose without containing any osmotic pressure control agent.

Significance of correcting the glucose concentration on the basis of the sodium ion concentration is described. Glucose is accumulated in the hydrogel layer in a state contained in the interstitial fluid. On the other hand, since the amount of the interstitial fluid exuded from the body varies according to the condition of the micropores provided in the horny layer, it is necessary to determine the amount of glucose taking into account the condition of the micropores formed. Since the sodium ion is considered to exist at substantially a fixed concentration in the body, the concentration of the sodium ion accumulated in the hydrogel layer after a certain extraction time has elapsed becomes high when, for example, the hole diameter of the micropores is large, and the concentration becomes low when the hole diameter is small. In other words, the concentration of the sodium ion in the interstitial fluid extracted reflects the condition of the micropores formed.

The hydrogel layer of the present invention is generally obtained by crosslinking by irradiation of radiation. According to the crosslinking by irradiation of radiation, a very clean hydrogel layer can be obtained because any chemical substance such as a crosslinking agent is not used unlike the chemical crosslinking. The crosslinking by irradiation of radiation can be carried out by a method, in which an aqueous solution of the hydrophilic polymer is applied on to a base to form a coating film, and the coating film is irradiated with radiation. When a group of plural rolls is used to move the base, and the coating of the aqueous solution of the hydrophilic polymer and the crosslinking by irradiation of radiation are conducted thereon, a sheet-like hydrogel layer can be continuously prepared. Therefore, when the crosslinking method by irradiation of radiation is adopted, the hydrogel layer can be continuously mass-produced.

Polyvinyl alcohol (PVA) prior to crosslinking has a saponification degree within a range of generally from 78 to 100 mol %, preferably from 97 to 100 mol % and an average polymerization degree within a range of from 500 to 4,000, preferably from 1,000 to 3,000, more preferably from 1,200 to 2,500. If the saponification degree of PVA is too low, the crosslinking reaction does not sufficiently progress, and the interstitial fluid-extracting ability of the resulting hydrogel layer is lowered. If the average polymerization degree of PVA is too low, the viscosity of an aqueous solution of such PVA becomes too low. When the aqueous solution of such PVA is applied on to a base, such problem that cis sing occurs, and the thickness of the resulting coating film becomes uneven may be caused in some cases. If the average polymerization degree of PVA is too high, its solubility in water is lowered, and it is difficult to prepare an aqueous solution having a moderate concentration.

When heating and stirring are conducted upon the preparation of the aqueous solution of PVA, an aqueous solution of PVA having a moderate concentration can be obtained even when PVA having a high average polymerization degree is used. However, deterioration by heat and yellowing are liable to occur. The saponification degree and average polymerization degree of PVA can be measured according to the methods known per se in the art. In case of a commercially available product, a cataloged value (indicated value) may be used.

The concentration of PVA in the aqueous solution of PVA is within a range of preferably from 7 to 30% by weight, more preferably from 7 to 20% by weight, particularly preferably from 7.5 to 15% by weight. In many cases, the concentration of PVA is controlled within a range of from 9 to 15% by weight, whereby good results can be obtained.

If the concentration of PVA in the aqueous solution of PVA is too low, cis sing occurs, and difficulty is encountered on the formation of a coating film even in thickness when such an aqueous solution of PVA is applied on to a base. If the concentration of PVA is too low, there is a strong tendency for the crosslinking by irradiation of radiation to be inhibited when an osmotic pressure control agent (for example, 80 mM of KCl) in an amount necessary for isotonicity between the hydrogel layer and the human skin is added into the aqueous solution of PVA, in addition to the above-described problems.

If the concentration of PVA in the aqueous solution of PVA is too high, the viscosity of such aqueous solution of PVA becomes too high, and so it is necessary to make the viscosity of the aqueous solution of PVA low by heating the aqueous solution upon coating. Thus, deterioration by heat and yellowing are liable to occur. If the concentration of PVA is too high, it is difficult to obtain hydrogel having a sufficient water content after the crosslinking by irradiation of radiation, in addition to the above-described problems.

Polyvinyl pyrrolidone (PVP) has an average polymerization degree within a range of from 20,000 to 150,000, preferably from 25,000 to 120,000. The concentration of PVP in the aqueous solution of PVP is within a range of preferably from 7 to 30% by weight, more preferably from 7 to 20% by weight, particularly preferably from 7.5 to 15% by weight. In many cases, the concentration of PVP is controlled within a range of from 9 to 15% by weight, whereby good results can be obtained.

PVP may be used by itself. However, it is preferably used in combination with PVA. A weight ratio of PVA:PVP is within a range of generally from 9:1 to 1:9, preferably from 8:2 to 2:8, more preferably from 8:2 to 5:5.

In order to form a hydrogel layer with a hydrophilic polymer composed of PVA and/or PVP, an aqueous solution of the hydrophilic polymer is applied on to a base, and the resultant coating film is irradiated with radiation to crosslink the hydrophilic polymer. No particular limitation is imposed on the base so far as the aqueous solution of the hydrophilic polymer can be applied thereto to form a coating film. However, examples thereof include glass and synthetic resin films. When a radiation-permeable synthetic resin film is used as the base, the base can be irradiated with radiation not only from an upper side of the base but also from a lower side of the base.

The radiation used in the present invention means particle-rays such as α-ray (particle-ray of an atomic nucleus of helium-4 emitted from a radioactive nuclide conducting α-disintegration), β-ray (negatron and positron emitted from an atomic nucleus) and electron ray (electron beam having almost fixed kinetic energy; generally produced by accelerating thermoelectrons in vacuum; and ionizing radiations such as γ-ray (electromagnetic radiation short in wavelength emitted and absorbed by transition between energy levels of atomic nuclei or elementary particles, or pair annihilation or pair production of elementary particles). In the present invention, ultraviolet ray is not included in the radiation. In the present invention, electron beam and γ-ray among the radiations are preferred from the viewpoints of workability and handling ability upon a production step of the hydrogel layer, with the electron beam being more preferred.

The irradiation of the electron beam can be conducted by means of a general-purpose electron beam irradiation apparatus. However, to the contrary, the production of the hydrogel layer is restricted by the characteristics of the electron beam irradiation apparatus. For example, regarding an absorbed dose at the surface when a coating film of the aqueous solution of PVA is irradiated with the electron beam by means of an electron beam irradiation apparatus, the accelerating voltage of which is 300 kV, as 100%, the relative dose is attenuated to about 50% at a deep portion of 300 μm. In an electron beam irradiation apparatus, the accelerating voltage of which is 800 kV, the relative dose is attenuated to about 30% at a deep portion of 2,500 μm. The relation between the accelerating voltage and the attenuation of the relative dose is not a linear proportional relation. When the relative dose at a deep portion is attenuated, the effect of crosslinking by irradiation of the electron beam is lowered at this portion. In order to conduct uniform crosslinking, it is desirable that the irradiation is conducted at such an accelerating voltage as to achieve a high relative dose, or the thickness of the coating film is controlled.

The irradiation dose of the electron beam is preferably selected from a range of from 5 to 20,000 kGy. An optimum value of the irradiation dose of the electron beam greatly varies depending on the accelerating voltage, properties of a subject to be irradiated, etc. For example, when electron beam of 200 kV in accelerating voltage is irradiated at an irradiation dose of 40 kGy, and γ-ray is then irradiated at 25 kGy, a good hydrogel layer can be formed.

The irradiation dose relates to a crosslinking density of the hydrogel layer. The larger the irradiation dose, the higher the crosslinking degree. It is preferable that electron beam, whose accelerating voltage is within a range of from 200 kV to 10 MV and whose irradiation dose is within a range of from 5 to 20,000 kGy, is irradiated to conduct crosslinking. The irradiation dose is preferably 15 to 3,000 kGy, more preferably 20 to 2,000 kGy when the accelerating voltage is 200 to 800 kV, and the thickness of the coating film is of the order of 70 to 500 μm though it varies according to the accelerating voltage and the thickness of the coating film. The irradiation of the electron beam is generally conducted under an atmosphere of an inert gas such as nitrogen for avoiding the generation of ozone and improving the reaction efficiency.

When the thickness of the coating film of the aqueous solution of the hydrophilic polymer is great, it is possible to raise the accelerating voltage or increase the irradiation dose. When a process, in which an aqueous solution of a hydrophilic polymer is applied on to a base, the coating film formed is irradiated with radiation to conduct crosslinking, a coating film of a new aqueous solution of the hydrophilic polymer is then formed on the hydrogel layer obtained by the crosslinking, and this coating film is irradiated with the radiation, is adopted necessary times, a hydrogel layer having a desired total thickness can be formed.

When at least one osmotic pressure control agent selected from group consisting of potassium chloride, urea, glycine, alanine and proline is used, the relationship between the concentration of the hydrophilic polymer and the osmolarity of the osmotic pressure control agent is preferably controlled in such a manner that the crosslinking reaction by the irradiation of radiation is not inhibited. Whether the crosslinking reaction of the coating film of the aqueous solution of the hydrophilic polymer is inhibited or not can be judged by whether a water separation phenomenon is observed in the resulting hydrogel layer or not. When no water separation is observed in the hydrogel layer, it can be judged that a sufficient crosslinking reaction occurs.

Whether a water separation phenomenon occurs in the hydrogel layer or not can be judged by placing a hydrogel layer cut out into a size 7 mm wide, 12 mm long and 700 μm thick on a polyester film held in a flat state for 1 minute in a thermohygrostat of 23° C. in temperature and 55% in relative humidity and observing whether water separation is observed at the surface of the hydrogel layer and around it or not. The fact that no water separation is observed in the hydrogel layer means that the crosslinking reaction by the irradiation of radiation is not inhibited.

The relationship between the concentration of the hydrophilic polymer and the osmolarity of the osmotic pressure control agent is preferably controlled as the reference that no water separation is observed in the hydrogel layer. More specifically, an aqueous solution of a hydrophilic polymer prepared by controlling the concentration of the hydrophilic polymer within a range of from 7 to 30% by weight and containing at least one osmotic pressure control agent selected from group consisting of potassium chloride, urea, glycine, alanine and proline in a proportion that the osmolarity thereof falls within a range of from 0.05 to 0.94 osmoles in such a manner that a sodium ion is substantially not contained is used. Supposing that the concentration of the hydrophilic polymer is b % by weight, and the osmolarity of the osmotic pressure control agent is a osmoles, a coating film of an aqueous solution of the hydrophilic polymer, which satisfies the relationship represented by the following relational expression (A)

$$a \leq 0.1b - 0.6 \tag{A}$$

is irradiated with the radiation to conduct crosslinking, whereby a hydrogel layer free of inhibition of the crosslinking reaction can be formed. As the radiation, may be used one radiation selected from the group consisting of α-ray, β-ray and γ-ray.

Figure 19:
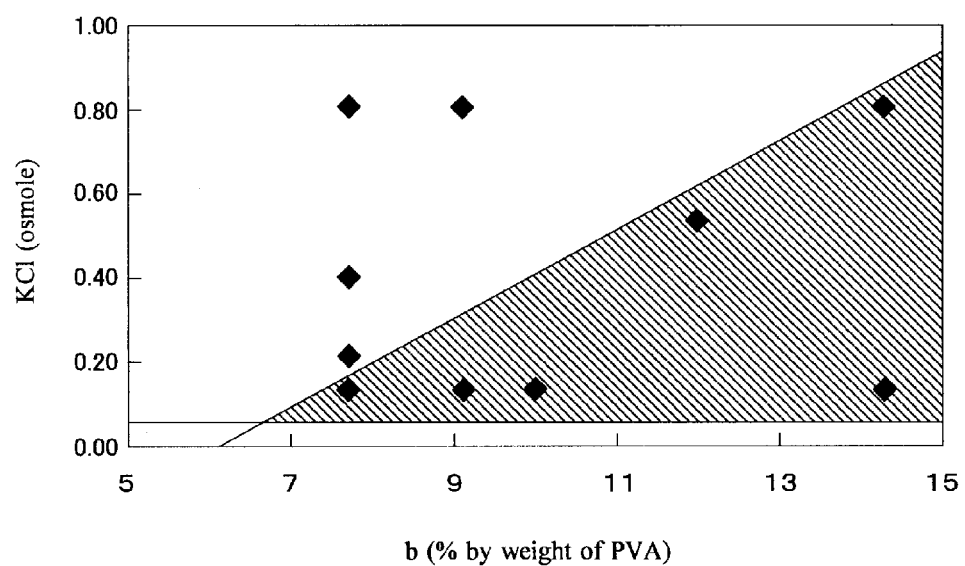
FIG. 19 is a graph illustrating the relationship between the osmolarity of KCl and the concentration of polyvinyl alcohol in a case where KCl was used as an osmotic pressure control agent in relation to whether separation of water from a hydrogel layer occurred or not.

FIG. 19 is a graph prepared on the basis of experimental data obtained by Examples 1 to 9 and Comparative Examples 1 to 4 in the present description. An abscissa of this graph indicates a concentration (b % by weight) of PVA in an aqueous solution of PVA, and an ordinate indicates an osmolarity (a osmoles) calculated out from the concentration (% by weight) of KCl. A case where no water separation was observed in the hydrogel layer obtained by irradiation of radiation (i.e., a case where the crosslinking reaction by the irradiation of the radiation is sufficient) and a case where water separation was observed are distinguished by an oblique line. A lower side of this oblique line indicates a region satisfying the relational expression (A). The concentration (b) of PVA is within a range of from 7 to 30% by weight, and the osmolarity (a) of KCl is within a range of from 0.05 to 0.94 osmoles.

Figure 20:
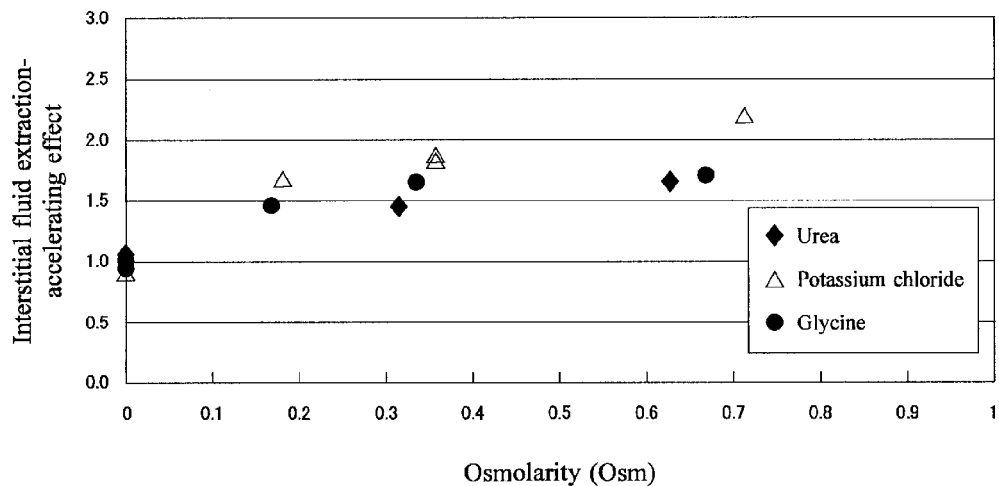
FIG. 20 is a graph illustrating the relationship between the concentration of each of various osmotic pressure control agents of urea, glycine and KCl and a ratio of a glucose extraction rate.
Figure 21:
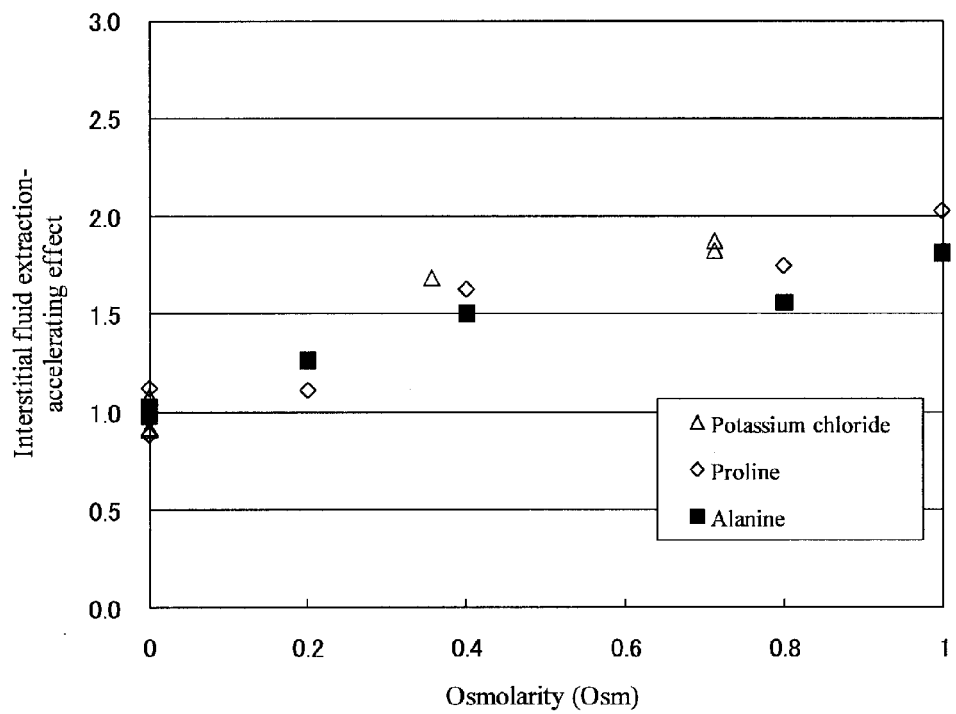
FIG. 21 is a graph illustrating the relationship between the concentration of each of various osmotic pressure control agents of alanine, proline and KCl and a ratio of a glucose extraction rate.

Urea, glycine, alanine and proline are evaluated as being substantially equivalent to KCl from the viewpoint of the function as the osmotic pressure control agent for the hydrogel layer of the present invention. This fact is apparent from experimental results in FIGS. 20 and 21. FIG. 20 is a graph illustrating the relationship between the osmolarity (osmoles) of each of potassium chloride (KCl), urea and glycine and an interstitial fluid extraction-accelerating effect. FIG. 21 is a graph illustrating the relationship between the osmolarity (osmoles) of each of potassium chloride (KCl), alanine and proline and an interstitial fluid extraction-accelerating effect.

The amount of the interstitial fluid extracted can be indicated by taking the amount of glucose percutaneously collected in a reserver as an index. Micropores extending to the horny layer were formed in the skin of a human upper arm, and a reserver (specifically, using a gel reserver formed from a PVA gel layer substantially containing no Na and having a size of 7 mm×12 mm and a base material layer of a PE film and a size of 28 mm×28 mm) was placed thereon. The extraction of the interstitial fluid was conducted according to the following procedure for evaluating the above-described 3 kinds of osmotic pressure control agents as to the interstitial fluid extraction-accelerating effect.

Procedure 1: Water (hereinafter may be referred to as "RO water") purified by reverse osmosis and having, the osmolarity of which is substantially zero, is put in a reserver to conduct extraction of an interstitial fluid over a predetermined period of time.

Procedure 2: Solutions of various osmolarities (for example, 0.3, 0.6, 1.2, 2.5 and 5.0 osmoles) are filled in the reserver by turns to conduct extraction of an interstitial fluid over a predetermined period of time.

Procedure 3: Lastly, RO water is put in the reserver to conduct extraction of an interstitial fluid over a predetermined period of time.

The concentration of glucose in the interstitial fluid collected in the reserver is measured by an enzyme method using a well-known glucose oxidase. The total amount (unit=ng) of glucose contained in the reserver is calculated out from the measured value of the glucose concentration. This total amount of glucose is divided by the extraction time (unit=min) to calculate out a glucose extraction rate (unit=ng/min). Supposing that the glucose extraction rate at each osmolarity of the osmotic pressure control agent is x, and an average value of the glucose extraction rates when RO water was used in Procedures 1 and 2 is y, the interstitial fluid extraction-accelerating effect of each osmotic pressure control agent can be calculated out by the following expression (B)

$$\text{Interstitial fluid extraction-accelerating effect} = x/y \quad (B)$$

As apparent from the results illustrated in FIG. 20, it is understood that urea and glycine exhibit substantially the same interstitial fluid extraction-accelerating effect as KCl. Accordingly, it can be understood that low-molecular organic compounds such as urea and glycine, which have the same effect as KCl, may also be used as the osmotic pressure control agent in place of KCl. As apparent from the results illustrated in FIG. 21, it is understood that alanine and proline exhibit substantially the same interstitial fluid extraction-accelerating effect as KCl. Accordingly, it can be understood that low-molecular organic compounds such as alanine and proline, which have the same effect as KCl, may also be used as the osmotic pressure control agent in place of KCl.

A better interstitial fluid extraction efficiency is exhibited as the water content in the hydrogel layer becomes higher. On the other hand, it is not preferable that the water content in the hydrogel layer is made excessively high from the viewpoints of suitability of the device for interstitial fluid extraction according to the present invention for the skin surface, releasability from the skin surface, physical strength upon measurement, etc. The water content in the hydrogel layer is within a range of preferably from 70 to 95% by weight, more preferably from 80 to 93% by weight, particularly preferably from 84 to 92% by weight.

In order to efficiently extract glucose and a sodium ion in the interstitial fluid, the swelling rate of the hydrogel layer is preferably controlled within a range of from 100 to 300%. The swelling rate of the hydrogel layer is a numerical value obtained by multiplying a value obtained by dividing a weight after immersing the hydrogel layer in physiological saline for 24 hours by a weight before the immersion in the physiological saline by 100.

It is effective that no sodium ion is substantially present in the hydrogel layer before the extraction of the interstitial fluid for conducting the measurement of interstitial fluid extracts. Therefore, the hydrogel layer is formed with a material substantially containing no sodium ion. When PVA is prepared, PVA can be generally obtained by saponifying polyvinyl acetate obtained by polymerizing a vinyl acetate monomer with a salt such as sodium chloride. Therefore, hydrogel of PVA obtained by dissolving commercially available PVA in an aqueous solution and crosslinking the resultant aqueous solution by irradiation of radiation generally comes to contain a sodium ion. Besides, when a significant amount of a sodium ion is contained in the hydrogel layer by some cause, the hydrogel layer is immersed in the aqueous solution used in the preparation of the PVA solution, and stirring is conducted, whereby the content of the sodium ion in the hydrogel layer can be reduced.

In order to impart flexibility to the hydrogel layer, a plasticizer such as glycerol, polyglycerol, polyethylene glycol (PEG) or polypropylene glycol (PPG) may be contained in the aqueous solution of the hydrophilic polymer in the production step of the hydrogel layer. Pharmacologically active substances such as an antibacterial agent may also be contained in the hydrogel layer in such a proportion that the crosslinking by the irradiation of the radiation is not inhibited. When an enzyme metabolizing an interstitial fluid component, such as a glucose oxidase, is contained in the hydrogel layer, it is difficult to stably collect the interstitial fluid component. Therefore, it is preferable that the hydrogel layer used in the present invention does substantially not contain an enzyme reacting with glucose, such as a glucose oxidase.

The thickness of the hydrogel layer is within a range of generally from 50 µm to 1.5 mm, preferably from 100 µm to 1 mm, more preferably from 300 to 900 µm. If the thickness of the hydrogel layer is too large, stress against the skin upon application of the device for interstitial fluid extraction becomes large, so that such inconveniences that a pressed trace is left on a portion where the hydrogel layer has come into contact with the skin, and a gap is made between the release layer and the pressure sensitive adhesive film (base material/pressure sensitive adhesive layer) to vaporize off water in the hydrogel layer are liable to occur. If the thickness of the hydrogel layer is too small, a back flow of glucose extracted occurs, and an interstitial fluid containing glucose in an amount necessary for analysis cannot be sufficiently collected.

In order to provide a hydrogel layer having a desired thickness, it is also possible to multi-layer the hydrogel layer. The multi-layering of the hydrogel layer can be achieved by adopting a method of laminating a plurality of hydrogel layers or a method, in which a hydrogel layer is formed by irradiating a coating film of an aqueous solution of a hydrophilic polymer with radiation in a step of irradiating with radiation, an aqueous solution of a hydrophilic polymer is then applied on to the hydrogel layer to form a coating film, and this coating film is irradiated with radiation. In the latter method, the process is repeated at least twice, whereby a multilayer hydrogel layer with each hydrogel layer uniformly crosslinked can be formed.

A portion of the hydrogel layer, with which the skin surface comes into contact, may be suitably changed according to a measuring instrument. However, it is generally preferable that its long side is 5 to 15 mm, and its short side is 3 to 10 mm. When the area (area of micropores) of a portion punctured by micro-needles is regarded as 100%, a contact area of the hydrogel layer with the skin is controlled to 50 to 200%, preferably 100 to 200% so as to cover the punctured portion.

The hydrogel layer is arranged on the substantial center of the pressure sensitive adhesive film (base material/pressure sensitive adhesive layer). The hydrogel layer desirably is desired to have good anchoring property so as to be held on the pressure sensitive adhesive film until the extraction of the interstitial fluid is completed. On the other hand, it is desired that the hydrogel layer can be easily peeled from the skin surface after completion of the extraction.

Examples of the release layer includes paper bases such as woodfree paper and glassine paper treated with a release agent such as a silicone resin, and sheets such as polyester films. As the release layer, may be used that used as release paper or release liner in the technical field of pressure sensitive adhesive tapes. Exposed surfaces of both pressure sensitive adhesive layer (exposed surface of the pressure sensitive adhesive layer) and hydrogel layer are covered with the release layer.

The device for interstitial fluid extraction according to the present invention has an area of a size that the pressure sensitive adhesive layer is exposed from around the hydrogel layer. The area of the hydrogel layer is equal to an area coming into contact with the skin surface. As described above, the device for interstitial fluid extraction according to the present invention can be caused to easily adhere to the skin by the construction that an adhesive surface capable of adhering to the skin is provided around the hydrogel layer, so that the device can be fixed to a desired skin surface without using a fitting device such as a belt, whereby the device for interstitial fluid extraction can relieve a burden to a user.

The pressure sensitive adhesive film 502 illustrated in FIG. 5a has a lower surface (pressure sensitive adhesive layer) having pressure sensitive adhesion property and an upper surface (base material layer composed of a synthetic resin film) having no pressure sensitive adhesion property and has a nature that water is not permeated. The pressure sensitive adhesive film 502 typically has a substantially square shape of a size of 28 mm×28 mm. The lower surface having pressure sensitive adhesion property has pressure sensitive adhesion property to a subject and the cartridge body 310. The hydrogel layer 501 is held on the substantial center of the pressure sensitive adhesive film 502 by adhering to the lower surface of the pressure sensitive adhesive film 502.

The pressure sensitive adhesive film 502 has a surface (pressure sensitive adhesive layer) having pressure sensitive adhesion property, whereby the hydrogel layer 501 can be held thereon, and the film can adhere to the skin in a state that the hydrogel layer 501 has been held. The pressure sensitive adhesive film 502 is composed of a material that water is not permeated, whereby vaporizing-off of water contained in the hydrogel layer 501 and water in the interstitial fluid collected can be prevented. Therefore, the area coming into contact with the skin can be prevented from being changed by vaporization of water in the hydrogel layer 501 during the collection of the interstitial fluid by the hydrogel layer 501, and so scattering of interstitial fluid extraction efficiency can be prevented.

The pressure sensitive adhesive film 502 has an area of the above-described size, whereby an opening in a gel receiving part 311 (see FIG. 6) can be blocked in such a manner that a liquid does not leak from the opening when the device for interstitial fluid extraction has been arranged in the gel receiving part 311 of the cartridge body 310. Notches 505, 505 for positioning upon sticking on the skin surface may be provided in the pressure sensitive adhesive film 502. A lead part (not illustrated) may also be provided at the pressure sensitive adhesive film 502.

Figure 5B:
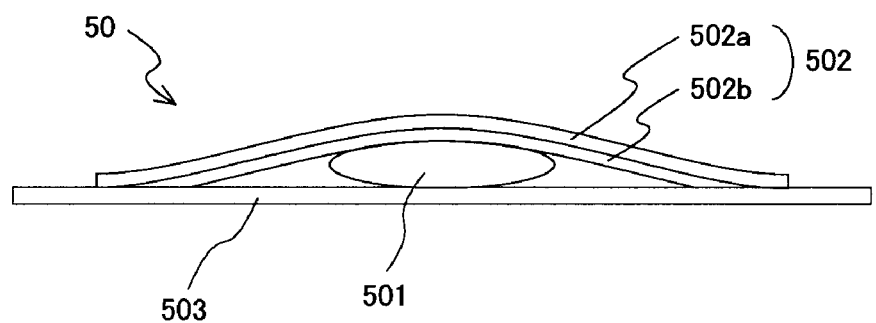
FIG. 5b is a cross-sectional view thereof.

FIG. 5b is a cross-sectional view illustrating a state of the device 50 for interstitial fluid extraction before use. The pressure sensitive adhesive film 502 is composed of a base material layer 502a formed from a synthetic resin film and a pressure sensitive adhesive layer 502b. The pressure sensitive adhesive film 502 is caused to adhere to a release layer 503 by an exposed surface of the pressure sensitive adhesive layer 502b in the state before use. The release layer 503 is so constructed that the hydrogel layer 501 and the pressure sensitive adhesive layer 502b present around it are exposed when the release layer is peeled upon use. The device for interstitial fluid extraction, from which the release layer 503 has been removed, is brought into close contact to the skin surface by the surface of the hydrogel layer 501 and the exposed surface of the pressure sensitive adhesive layer 502b.

The structure and function of the cartridge 30 for analysis will be described in more detail. As illustrated in FIG. 4, the cartridge 30 for analysis is equipped with a cartridge body 310 and reaction reagents 330 to glucose. The reaction reagents 330 include reaction reagents such as an enzyme [for example, glucose oxidase (abbreviated as "GOD")], which becomes a catalyst for glucose, an enzyme [peroxidase (abbreviated as "POD")], which becomes a catalyst for hydrogen peroxide ($H_2O_2$), and a coloring pigment, tetramethylbenzidine (3,3',5,5'-tetramethylbenzidine), reacting with an active oxygen (O*) formed from $H_2O_2$ by the presence of POD. The reaction reagents 330 to glucose have size and shape fittable into a reagent holding part 314 (FIG. 6) provided in the cartridge body 310.

The cartridge body 310 is a rectangular plate formed from a synthetic resin such as an acrylic resin colored by a pigment into, for example, black. The cartridge body 310 is formed of, for example, a rectangular plate 24 mm long, 56 mm wide and 3 mm thick, and the reaction reagents 330 to glucose are fitted into a recessed part (reagent holding part 314 in FIG. 6) formed in the surface thereof. A recessed part (gel receiving part 311 in FIG. 6) for receiving the hydrogel layer 501 of the device 50 for interstitial fluid extraction is formed in the surface of the cartridge body 310. The device 50 for interstitial fluid extraction is caused to adhere to the surface of the cartridge body 310 by the pressure sensitive adhesive layer while the hydrogel layer 501 is being received in the recessed part. A surface (an exposed surface in FIG. 4) of the cartridge body 310, to which the device 50 for interstitial fluid extraction adheres, is referred to as an upper surface, and a back surface thereof is referred to as a lower surface. The structure of the cartridge body 310 will hereinafter be described in more detail with reference to FIGS. 6 and 7.

FIGS. 6 and 7 are plan views of the cartridge body 310. In FIG. 6, the structures of the upper surface and lower surface of the cartridge body 310 are illustrated by a solid line and a broken line, respectively. In FIG. 7, the structures of the lower surface and upper surface of the cartridge body 310 are illustrated by a solid line and a broken line, respectively.

As illustrated in FIGS. 6 and 7, the cartridge body 310 is provided with a gel receiving part 311, inlet hole 312, upstream-side connection hole 313, reaction reagent holding part 314, storage part 317 for glucose detection, downstream-side connection hole 315 and discharge hole 316 as structures visible from the upper surface. The cartridge body 310 is provided with a first connection passage 321, storage part 322 for sodium detection and second connection passage 323 as structures visible from the lower surface. These respective parts are recessed parts or through-holes. Therefore, the cartridge body 310 can be produced by integrally molding a synthetic resin by injection molding or the like.

The cartridge body 310 forms one passage from the inlet hole 312 to the discharge hole 316 when arranged in the cartridge arranging part 12 of the analysis unit body 10. The inlet hole 312 is a circular hole extending through from the upper surface of the cartridge body 310 to the lower surface thereof, and the diameter thereof can be set to, for example, 0.7 mm. The inlet hole 312 is provided in such a manner that the injection nipple 141 provided in the cartridge arranging part 12 is located just under the hole in a vertical direction when the cartridge body 310 has been arranged in the cartridge arranging part 12 of the analysis unit body 10, whereby the recovery liquid is injected into the gel receiving part 311 through the inlet hole 312 when the cartridge body 310 has been arranged in the cartridge arranging part 12.

The gel receiving part 311 is a rectangular recessed part formed in the upper surface of the cartridge body 310 and has a size of, for example, 14 mm (long side)×9 mm (short side)×2 mm (depth). The inlet hole 312 is provided in a bottom surface of gel receiving part 311. The gel receiving part 311 has, for example, such a size as described above, whereby the hydrogel layer 501 held by the device 50 for interstitial fluid extraction and having a size of 12 mm (long side)×7 mm (short side)×0.7 mm (thickness) can be received.

The hydrogel layer 501 held by the device 50 for interstitial fluid extraction is received in the gel receiving part 311. Specifically, the device 50 for interstitial fluid extraction is arranged in the gel receiving part 311, whereby the pressure sensitive adhesive film 502 of the device 50 for interstitial fluid extraction adheres to a peripheral edge of the gel receiving part 311, and the hydrogel layer 501 held thereby is received in the gel receiving part 311 in a state dangled in a midair.

A stepped part 318 recessed deeper than the bottom surface of the gel receiving part 311 and the upstream-side connection hole 313 are provided at the bottom surface of the gel receiving part 311 and at a position on a diagonal line of the inlet hole 312. The upstream-side connection hole 313 is composed of a circular hole extending through from the upper surface of the cartridge body 310 to the lower surface thereof and having a diameter of, for example, 1.5 mm.

As illustrated in FIG. 7, the upstream-side connection hole 313 is opened in the bottom surface of the first connection passage 321 composed of a groove formed in the lower surface and having a depth of, for example, about 0.5 mm. The first connection passage 321 extends horizontally in a direction of the long side of the cartridge body 310 and is linked to the storage part 322 for sodium detection formed at the substantial center of the lower surface of the cartridge body 310.

The storage part 322 for sodium detection is composed of a circular groove having a depth of, for example, about 1.5 mm. The storage part 322 for sodium detection is provided so as to be located just above the sodium detection part 22 provided at the bottom surface of the cartridge arranging part 12 in a vertical direction when the cartridge body 310 has been arranged in the cartridge arranging part 12 of the analysis unit body 10. More specifically, the storage part 322 for sodium detection is provided in such a manner that the electrodes 222 for measurement of the sodium ion concentration of the sodium detection part 22 are located at a space surrounded by the plate-like member 221 and the storage part 322 for sodium detection.

The storage part 322 for sodium detection is linked to the second connection passage 323 composed of a groove having a depth of, for example, about 0.5 mm. The second connection passage 323 extends horizontally in a direction of the short side of the cartridge body 310 through a stepped part from the storage part 322 for sodium detection as an initial point, then turns its direction by 90° to extend horizontally in a direction of the long side, and further turns its direction by about 45° inward to extend horizontally. The downstream-side connection hole 315 is formed at the bottom of the distal end of the second connection passage 323. The downstream-side connection hole 315 is composed of a circular hole extending through from the upper surface of the cartridge body 310 to the lower surface thereof and having a diameter of, for example 0.7 mm.

As illustrated in FIG. 6, the reagent holding part 314 is provided at the upper surface of the cartridge body 310. The reagent holding part 314 is composed of a recessed part formed in the upper surface of the cartridge body 310 and having a depth of, for example, about 1 mm. The reagent holding part 314 is shaped into a substantially rectangular form long in the long side direction of the cartridge body 310.

The storage part 317 for glucose detection composed of a groove formed deeper than the reagent holding part 314 is provided at the reagent holding part 314. The downstream-side connection hole 315 is opened in the bottom surface of this storage part 317 for glucose detection. The storage part 317 for glucose detection is composed of a groove having a depth of about 1.5 mm from the bottom surface of the reagent holding part 314. The storage part 317 for glucose detection extends horizontally in a direction of the short side of the cartridge body 310 from a position where the downstream-side connection hole 315 is opened as an initial point, then turns its direction by 90° to extend horizontally in a direction of the long side, further turns its direction by 90° inward to extend horizontally in the short side direction, and then further turns its direction by 90° to extend horizontally in the long side direction. The discharge hole 316 is formed at the distal end of the storage part 317 for glucose detection.

The discharge hole 316 is a circular hole extending through from the upper surface of the cartridge body 310 to the lower surface thereof and having a diameter of, for example, 0.7 mm. The discharge hole 316 is provided in such a manner that the discharge nipple 151 provided in the cartridge arranging part 12 is located just under the hole in a vertical direction when the cartridge body 310 has been arranged in the cartridge arranging part 12 of the analysis unit body 10, whereby the recovery liquid is discharged from the discharge nipple 151 through the discharge hole 316 when the cartridge body 310 has been arranged in the cartridge arranging part 12.

The inlet hole 312 is linked to the upstream-side connection hole 313 through the gel receiving part 311. The upstream-side connection hole 313 is linked to the downstream-side connection hole 315 through the first connection passage 321, the storage part 322 for sodium detection and the second connection passage 323. More specifically, the upstream-side connection hole 313 is linked to the downstream-side connection hole 315 in the lower surface through a series of grooves having a depth and a width, which permit a liquid passing through between a horizontal plane and the lower surface of the cartridge body 310 when the cartridge body 310 is placed on the horizontal plane. The downstream-side connection hole 315 is linked to the discharge hole 316 through the storage part 317 for glucose detection. Therefore, the cartridge body 310 forms one passage from the inlet hole 312 to the discharge hole 316 when placed on the horizontal plane.

Figure 8:
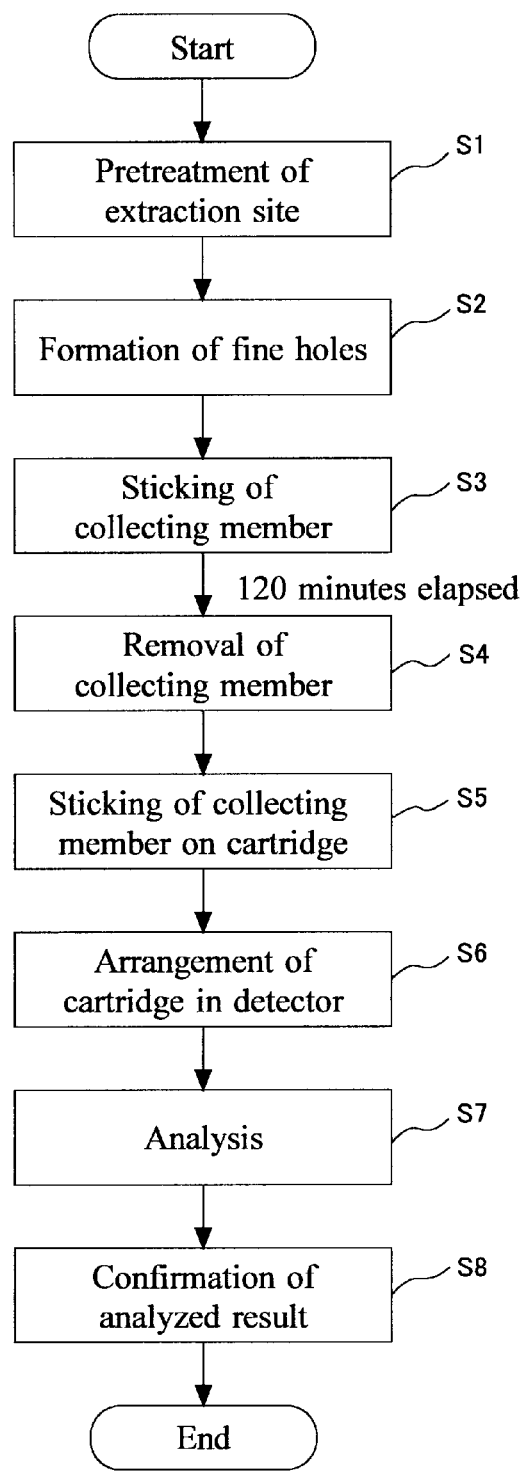
FIG. 8 is a flow chart explaining an exemplary biocomponent analyzing process using the biocomponent analysis unit.

The function of the cartridge 30 for analysis will hereinafter be described together with the operation of the analysis unit body 10. FIG. 8 is a flow chart illustrating a biocomponent analyzing process using a biocomponent analysis unit according to this embodiment. In Step S1, a subject is subjected to a pretreatment of a site, from which an interstitial fluid is collected, more specifically, alcohol washing. Substances (sweat, dust, etc.) attached to the skin, which form disturbance factors of analysis, are removed by the alcohol washing.

In Step S2, micropores are formed in the collection site washed with alcohol as a permeability-improving treatment. The micropores are holes extending through the horny layer of the skin and having such a depth as may extend up to a boundary between the interior of the epidermis and the dermis, but does not extend up to a deep site of the dermis. The treatment for forming such micropores can be conducted by means of, for example, the fine hole forming device described in US2007/0233011 A1. The extraction and collection of an interstitial fluid from the subcutaneous tissue can be thereby accelerated without being followed by bleeding.

In Step S3, the device 50 for interstitial fluid extraction is stuck on the collection site in which the micropores have been formed. More specifically, the hydrogel layer 501 contained in the device 50 for interstitial fluid extraction is brought into contact with the skin in such a manner that the skin site, in which the micropores have been formed, is covered with the hydrogel layer 501. The pressure sensitive adhesive film 502 holding the hydrogel layer 501 is caused to adhere to around the skin site in which the micropores have been formed. The device 50 for interstitial fluid extraction is left to stand for a predetermined period of time of at least 120 minutes in a state stuck on the skin in this manner to extract an interstitial fluid exuded from the skin, in which the micropores have been formed, and collect it in the hydrogel layer 501.

After the predetermined period of time has elapsed after the device 50 for interstitial fluid extraction was stuck on the skin, the process is advanced to Step S4 to take the device 50 for interstitial fluid extraction out of the skin.

In Step S5, the device 50 for interstitial fluid extraction taken out of the skin is stuck on the cartridge 30 for analysis.

In Step S6, the cartridge 30 for analysis, on which the device 50 for interstitial fluid extraction has been stuck, is arranged in the cartridge arranging part 12 of the analysis unit body 10. The cartridge 30 for analysis is arranged in such a manner that the storage part 322 for sodium detection faces the bottom surface of the cartridge arranging part 12. After the cartridge 30 for analysis has been arranged in the analysis unit body 10, the movable top plate 13 of the analysis unit body 10 is closed. Since the movable top plate 13 is biased toward a direction to be closed, the cartridge 30 for analysis arranged in the cartridge arranging part 12 is pressed from above by the movable top plate 13 in a state surrounded by the injection nipple 141, the discharge nipple 151, the sodium detection part 22 and the movable top plate 13.

In Step S7, analysis of a biocomponent is conducted on the basis of the interstitial fluid collected. Specifically, a user operates the operation part 24 of the analysis unit body 10 in a state that the cartridge 30 for analysis has been arranged in the cartridge arranging part 12 to direct beginning of analysis of the biocomponent to the control part 25. The control part 25, to which the beginning of analysis has been directed, execute a predetermined program, thereby conducting the analysis of the biocomponent. The analysis of the biocomponent includes analysis of a glucose concentration by cooperation of the glucose detection part 21 and the control part 25, and analysis of a sodium ion concentration by cooperation of the sodium detection part 22 and the control part 25.

After the analysis of the biocomponent by the analysis unit body 10 has been completed, analytical results are displayed on the display part 23. In Step S8, the subject confirms the analytical results displayed on the display part 23, thereby completing a series of analyzing steps.

Figure 9:
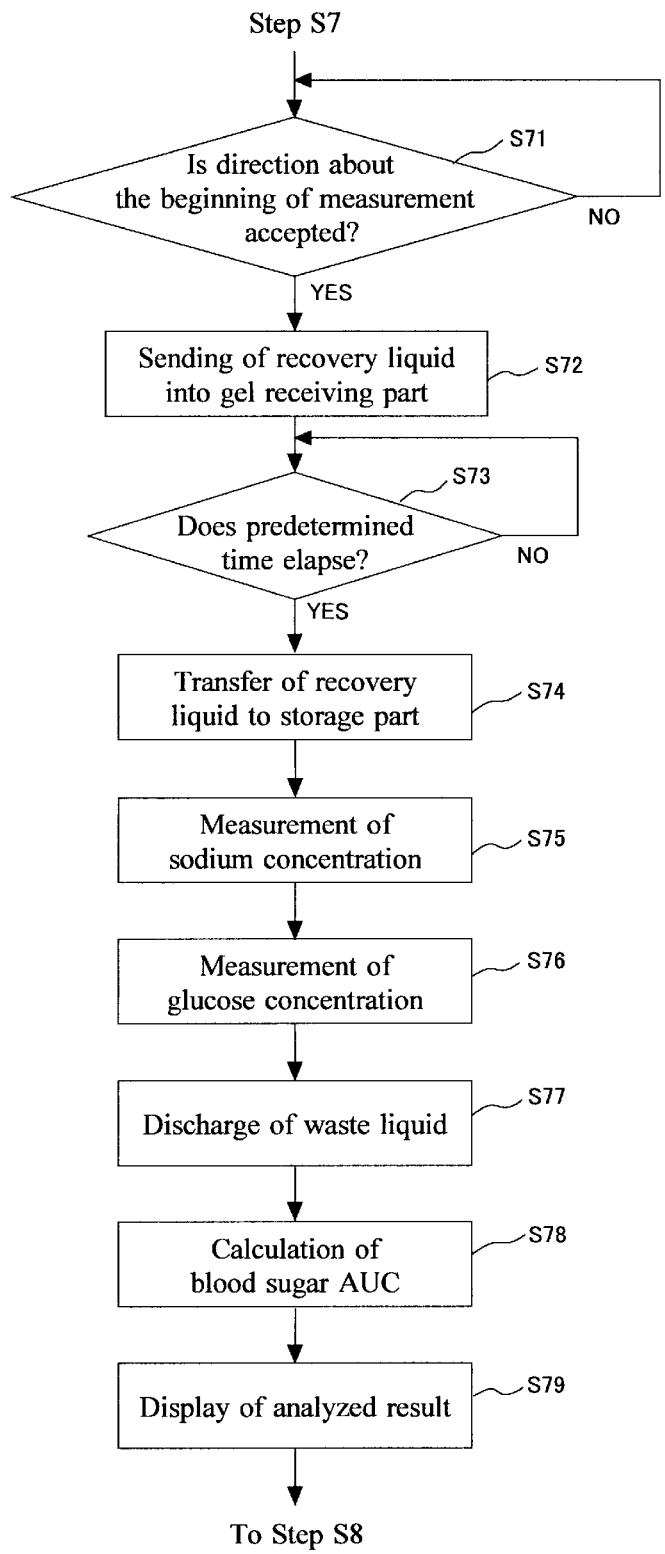
FIG. 9 is a flow chart for explaining the process of Step S7 in FIG. 8.
Figure 10:
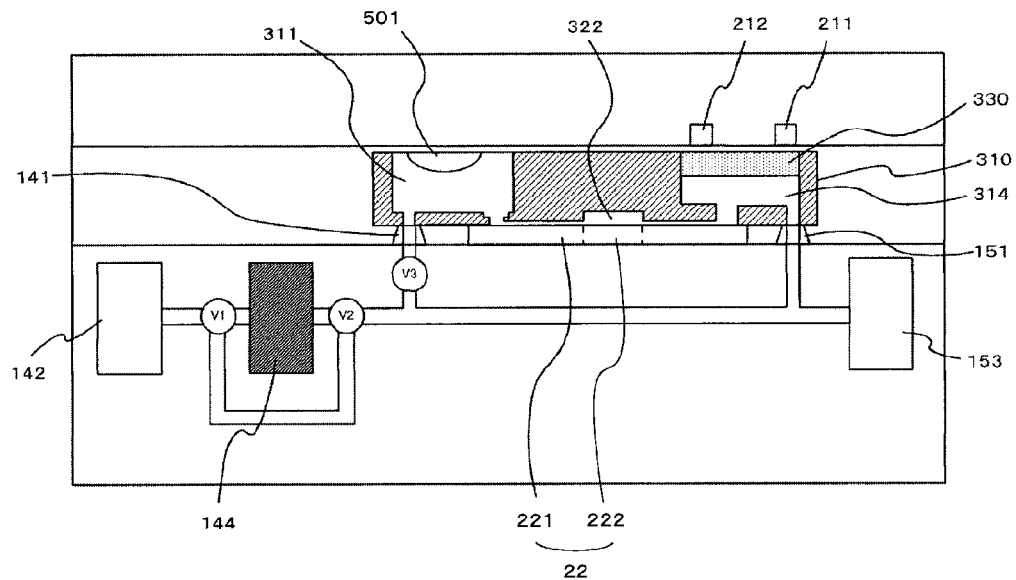
FIG. 10 is a typical cross-sectional view for explaining the operation of the biocomponent analysis unit illustrated in FIG. 1.
Figure 11:
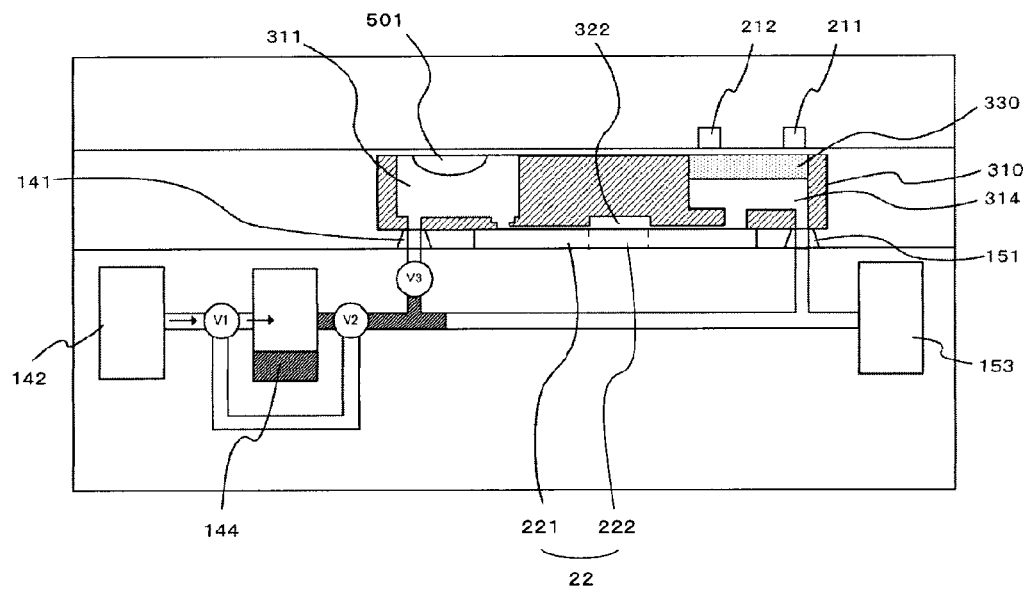
FIG. 11 is a typical cross-sectional view for explaining a particular operation in the biocomponent analysis unit illustrated in FIG. 1.
Figure 12:
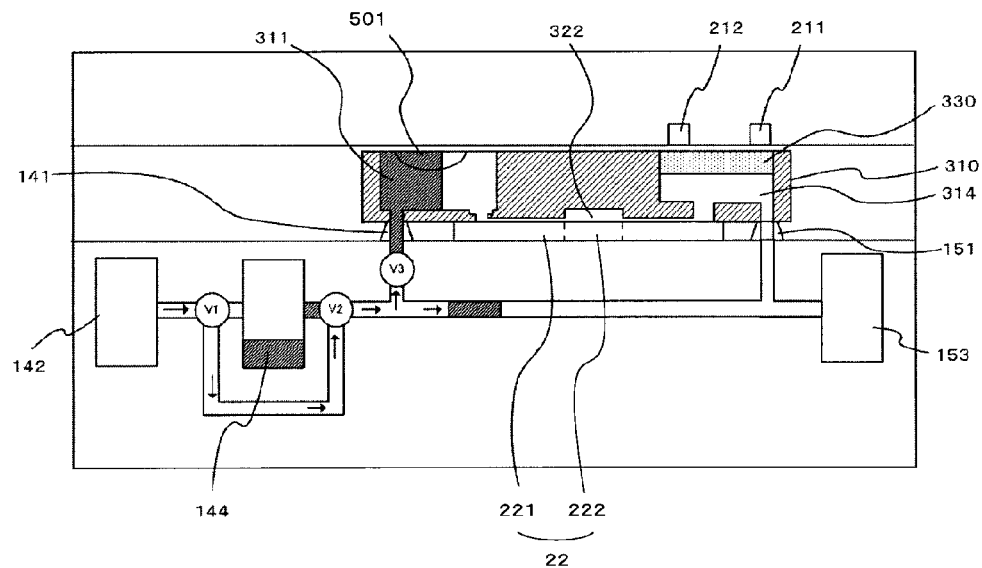
FIG. 12 is a typical cross-sectional view for explaining a particular operation in the biocomponent analysis unit illustrated in FIG. 1.

FIG. 9 is a flow chart for explaining the process of Step S7 in FIG. 8. A program for realizing the step shown herein is stored in ROM contained in the control part 25. CPU of the control part 25 executes the program stored in ROM, thereby executing the step shown in this flow chart.

FIG. 10 to FIG. 16 are typical cross-sectional views for explaining the operation of the biocomponent analysis unit according to this embodiment, and the flow of a recovery liquid is illustrated with time in order of these drawings. These drawings illustrate a state that the cartridge 30 for analysis has been arranged in the cartridge arranging part 12, the recovery liquid is indicated by black, and the flow of air sent by the pump 142 is indicated by an arrow. The operating principle of the analysis unit is described on the basis of FIG. 9, and FIGS. 10 to 16.

In Step S71 of FIG. 9, the control part 25 judges whether direction about the beginning of analysis by the user has been accepted or not. When the control part 25 judges that the direction about the beginning of analysis has been accepted ("YES" in Step S71), the process is advanced to Step S72. When the control part 25 judges that the direction about the beginning of analysis has not been accepted ("NO" in Step S71), the process is returned to Step S71.

In Step S72, the control part 25 executes a process of injecting a recovery liquid for recovering a biocomponent in the interstitial fluid collected in the hydrogel layer 501. Specifically, the control part 25 executes a process of controlling the electromagnetic valve V1 to connect the upstream-side passage 143 to the pump 142, controlling the electromagnetic valve V2 to connect the pump 142 to the downstream-side passage 145 and controlling the electromagnetic valve V3 to shut down the connection between the downstream-side passage 145 and the injection nipple 141. The control part 25 then executes a process of sending air to the passages by driving the pump 142 by a motor (not illustrated). The recovery liquid stored in the recovery liquid tank 144 is thereby pressed out to the downstream-side passage 145 and the waste liquid passage 147 to fill the passage from the electromagnetic valve V2 to the electromagnetic valve V3 with the recovery liquid pressed out (see FIGS. 2, 10 and 11).

After the control part 25 has stopped the drive of the pump 142, the control part 25 executes a process of controlling the electromagnetic valve V1 to connect the upstream-side passage 143 to the bypass passage 146, controlling the electromagnetic valve V2 to connect the bypass passage 146 to the downstream-side passage 145 and controlling the electromagnetic valve V3 to open the connection between the downstream-side passage 145 and the injection nipple 141. A series of passages from the pump 142 to the injection nipple 141 through the bypass passage 146 is thereby formed.

The control part 25 executes a process of driving the pump 142 again to send air to the passages. The air sent from the pump 142 is thereby passed through the upstream-side passage 143, the bypass passage 146 and the downstream-side passage 145 and send to the injection nipple 141. At the time the opening and closing of the electromagnetic valves V2 and V3 have been changed over, the passage from the electromagnetic valve V2 to the electromagnetic valve V3 is filled with a predetermined amount of the recovery liquid. The air is sent from the pump 142, whereby the predetermined amount of the recovery liquid stored between the electromagnetic valve V2 and the electromagnetic valve V3 is pressed out toward the injection nipple 141, and the recovery liquid flowed in the waste liquid passage 147 is pressed out toward the waste liquid tank 153 (see FIG. 12).

The injection nipple 141 is arranged so as to link to the inlet hole 312 of the cartridge 30 for analysis arranged in the cartridge arranging part 12. The recovery liquid sent toward the injection nipple 141 is injected into the gel receiving part 311 through the injection nipple 141 and the inlet hole 312.

When the recovery liquid is injected into the gel receiving part 311, the gel receiving part 311 is being filled with the recovery liquid. If the recovery liquid is transferred toward the upstream-side connection hole 313 from the inlet hole 312 at the shortest distance, the recovery liquid is first held by the stepped part 318 due to surface tension before leaked out of the upstream-side connection hole 313 because the periphery of the upstream-side connection hole 313 is surrounded by the stepped part 318 higher by a step than the opening face of the upstream-side connection hole 313. Therefore, the recovery liquid is pressurized in a direction spreading in the gel receiving part 311 rather than a direction leaking out of the upstream-side connection hole 313 so far as a pressure higher than the surface tension applied to the stepped part 318 is not applied. Accordingly, the recovery liquid injected spreads in the whole of the gel receiving part 311 without leaking out of the upstream-side connection hole 313 (see FIG. 12). Lowering of analytical precision caused by filling the gel receiving part 311 with the recovery liquid in an uneven state can be thereby prevented.

Figure 13:
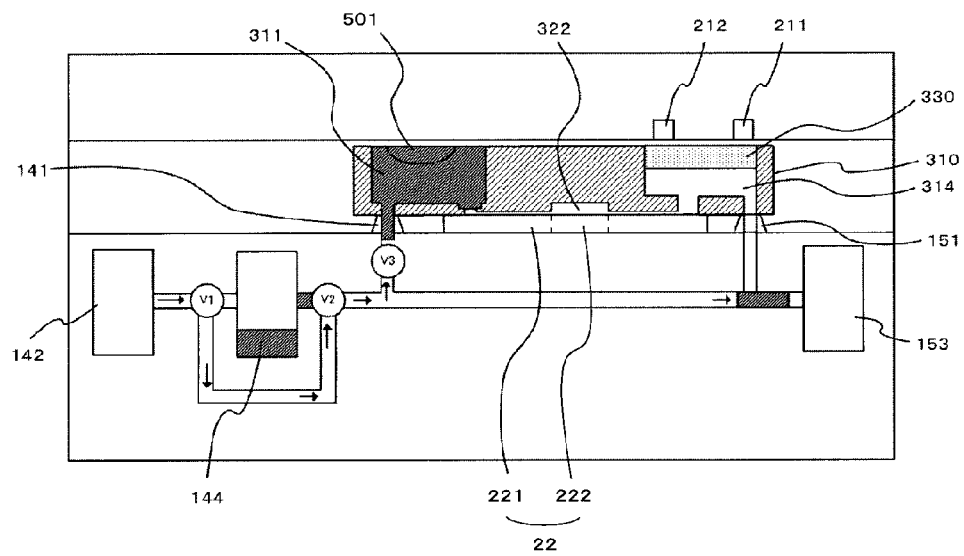
FIG. 13 is a typical cross-sectional view for explaining a particular operation in the biocomponent analysis unit illustrated in FIG. 1.

When all the predetermined amount of the recovery liquid is injected into the gel receiving part 311, the hydrogel layer 501 is embedded in the recovery liquid (see FIG. 13). The control part 25 temporally stops the drive of the pump 142 at the time the injection of the predetermined amount of the recovery liquid has been completed. Even when the drive of the pump 142 is stopped, the recovery liquid does not flow backward because an air pressure is applied to the liquid facing the inlet hole 312 from a lower side. Since the passage is maintained at a certain air pressure by stopping the drive of the pump 142, the recovery liquid filled in the gel receiving part 311 is held in a state stored in the gel receiving part 311 without leaking out of the upstream-side connection hole 313.

In Step S73 of FIG. 9, the control part 25 judges whether a predetermined period of time (for example, 10 minutes) has elapsed from the completion of the injection of the recovery liquid or not. When the control part 25 judges that the predetermined period of time has elapsed ("YES" in Step S73), the process is advanced to Step S74. When the control part 25 judges that the predetermined period of time has not elapsed ("NO" in Step S73), the process is returned to repeat the process of S73 until the predetermined period of time has elapsed.

The hydrogel layer 501 is left to stand for the predetermined period of time in a state embedded in the recovery liquid in this manner, whereby the interstitial fluid collected in the hydrogel layer 501 sufficiently diffuses into the recovery liquid.

In Step S74 of FIG. 9, the control part 25 executes a process of transferring the recovery liquid stored in the gel receiving part 311 to the storage part 322 for sodium detection and the storage part 317 for glucose detection. Specifically, the control part 25 controls the pump 142 in such a manner that air of the same volume as the gel receiving part 311 is sent to the gel receiving part 311. When the air is sent to the gel receiving part 311, a pressure higher than the surface tension is applied to the liquid facing the upstream-side connection hole 313, and the recovery liquid stored in the gel receiving part 311 is caused to flow out to the first connection passage 321 through the upstream-side connection hole 313.

When the air is further sent to the gel receiving part 311, the recovery liquid flowed out to the first connection passage 321 reaches the storage part 322 for sodium detection to fill the storage part 322 for sodium detection with the recovery liquid. When the air is still further sent to the gel receiving part 311, the recovery liquid reaches the storage part 317 for glucose detection through the downstream-side connection hole 315. The recovery liquid sent to the storage part 317 for glucose detection comes into contact with the reaction reagents 330 to glucose held by the reagent holding part 314 (see FIG. 14).

The construction that the recovery liquid stored in the gel receiving part 311 is sent to a position different from the gel receiving part 311 is adopted, whereby the recovery liquid is agitated. Therefore, even if the biocomponent transferred into the gel receiving part 311 unevenly diffuses into the recovery liquid, the concentration distribution of the biocomponent in the recovery liquid can be made even by agitating the recovery liquid.

In Step S75 of FIG. 9, the control part 25 executes a process of stopping the drive of the pump 142 and measuring a sodium concentration.

Figure 14:
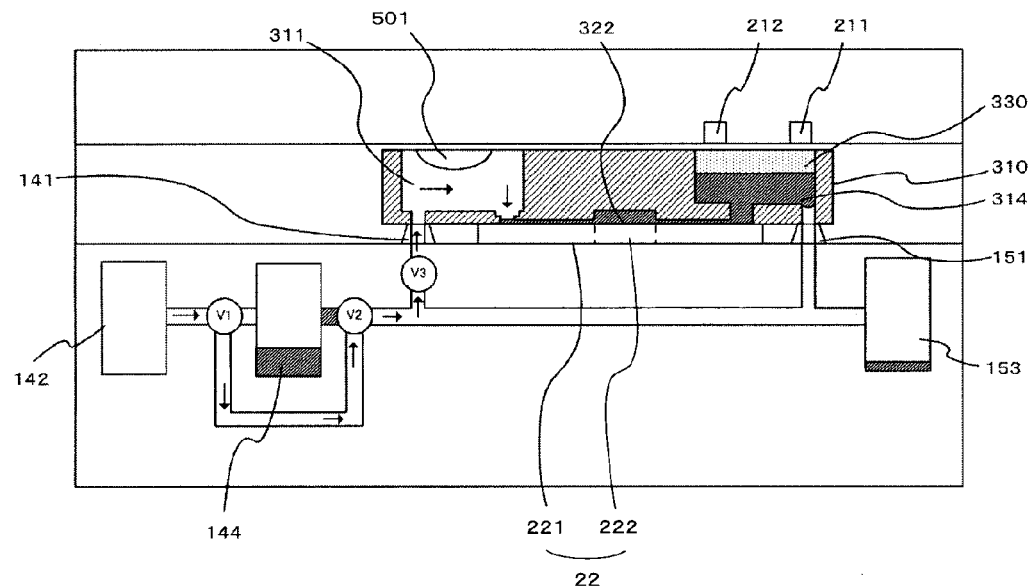
FIG. 14 is a typical cross-sectional view for explaining a particular operation in the biocomponent analysis unit illustrated in FIG. 1.
Figure 15:
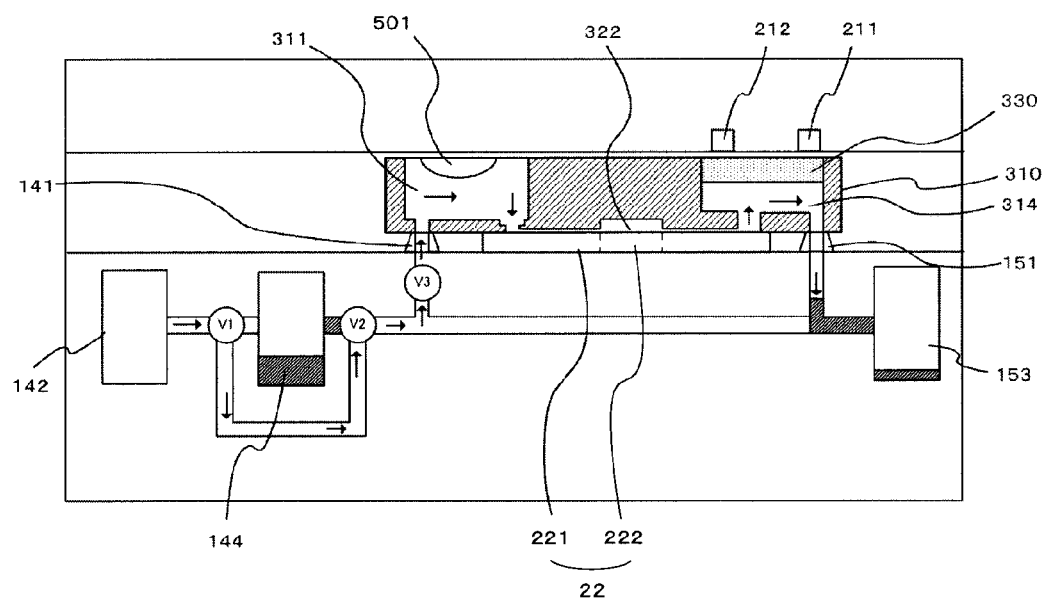
FIG. 15 is a typical cross-sectional view for explaining a particular operation in the biocomponent analysis unit illustrated in FIG. 1.
Figure 16:
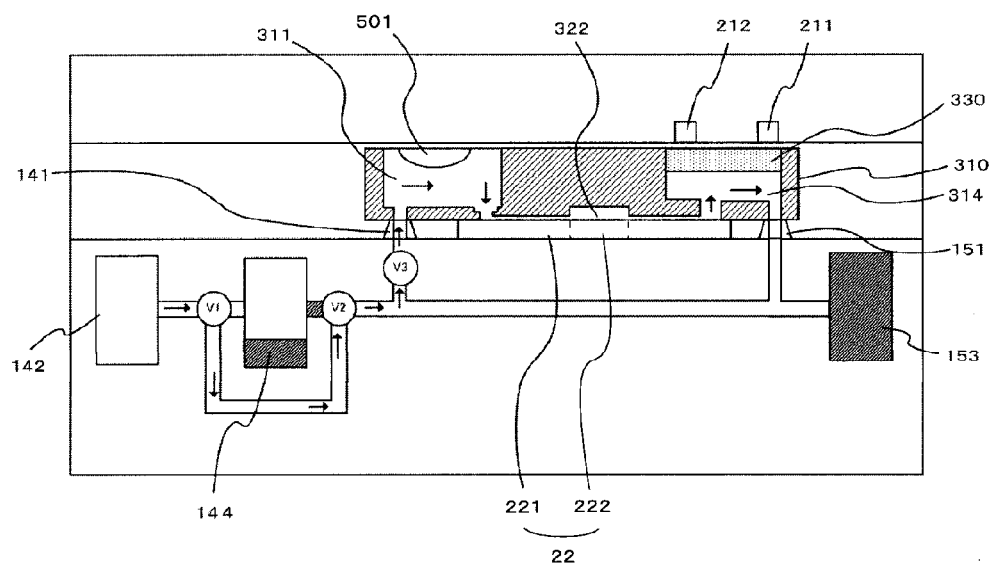
FIG. 16 is a typical cross-sectional view for explaining a particular operation in the biocomponent analysis unit illustrated in FIG. 1.

As illustrated in FIG. 14, the sodium detection part 22 provided at the bottom surface of the cartridge arranging part 12 forms a closed space with the storage part 322 for sodium detection provided at the lower surface of the cartridge 30 for analysis. The sodium detection part 22 is equipped with the electrodes 222 for measurement of a sodium ion concentration provided so as to be exposed to the surface. When the recovery liquid is stored in the storage part 322 for sodium detection, the electrodes 222 for measurement of a sodium ion concentration are in a state completely immersed in the recovery liquid stored. In this state, the control part 25 apply a fixed current to the electrodes 222 for measurement of a sodium ion concentration to acquire a voltage value and to obtain a sodium ion concentration "$C_{Na}$" on the basis of the thus-obtained voltage value and a calibration curve stored in the control part 25 in advance.

In Step S76 of FIG. 9, the control part 25 executes a process of measuring a glucose concentration. The light source 211 and the light reception part 212 are provided at the surface of the movable top plate 13, which faces the cartridge 30 for analysis. As illustrated in FIG. 14, the reaction reagents 330 to glucose are held in the reagent holding part 314 of the cartridge body 310. The reaction reagents 330 are immersed in the recovery liquid. Glucose transferred into the recovery liquid undergoes the following chemical reactions with GOD, $H_2O_2$, POD and the coloring pigment contained in the reaction reagents 330. As a result, the reaction reagents 330 change a color.

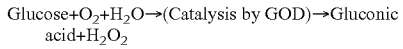

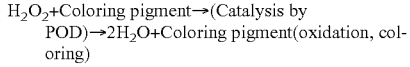

As apparent from the above reaction formulae, the degree of coloring of the coloring pigment is proportional to the amount of glucose. Thus, the degree of color change of the coloring pigment is optically detected, whereby the glucose concentration can be obtained.

In this embodiment, the glucose detection part is so constructed that the reaction reagents 330 are irradiated with light of a wavelength high in absorption efficiency by a color after color change of the coloring pigment from the light source 211. The light reception part 212 is so constructed that reflected light of the light irradiated by the light source 211 is received. The control part 25 acquires a glucose concentration "$C_{Glc}$" on the basis of a difference in quantity between the quantity of light received by the light reception part 212 before coloring of the coloring pigment and the quantity of light received by the light reception part 212 after coloring of the coloring pigment.

In Step S77 of FIG. 9, the control part 25 executes a process of sending the recovery liquid stored in the cartridge 30 for analysis to the liquid discharge part 15. Specifically, the control part 25 executes a process of sending air to the storage part 322 for sodium detection and the storage part 317 for glucose detection by driving the pump 142 again. The air send presses out the recovery liquid toward the passage 152 through the discharge nipple 151 (see FIG. 15). The recovery liquid pressed out is stored in the waste liquid tank 153 through the passage 152 (see FIG. 16).

In Step S78 of FIG. 9, the control part 25 applies the resultant sodium ion concentration "$C_{Na}$" and glucose concentration "$C_{Glc}$" to the following equation (1) to acquire blood sugar AUC and stores the blood sugar AUC thus obtained in ROM.

[Numerical Formula 1]

$$AUC=(C_{Glc} \times E+F) \times t/(C_{Na} \times G+H) \quad (1)$$

In the equation, t is a time required to collect an interstitial fluid, and in this embodiment, t is set to 60 minutes temporarily. E, F, G and H are constants.

In Step S79 of FIG. 9, the control part 25 displays the blood sugar AUC obtained in Step S78 on the display part 23 and advances the process to Step 8

A measuring principle of a measuring method of a blood sugar AUC value is described with reference to FIGS. 17 and 18. In general, the glucose concentration [IG(t)] in an interstitial fluid exhibits good followability for the glucose concentration [BG(t)] in the blood, and it is known that the glucose concentration [IG(t)] in the interstitial fluid and the glucose concentration [BG(t)] have strong correlation. The glucose concentration [IG(t)] in the interstitial fluid can be represented by the following equation (2) using a constant α.

[Numeral Formula 2]

$$BG(t) = \alpha \times IG(t) \quad (2)$$

Figure 17:
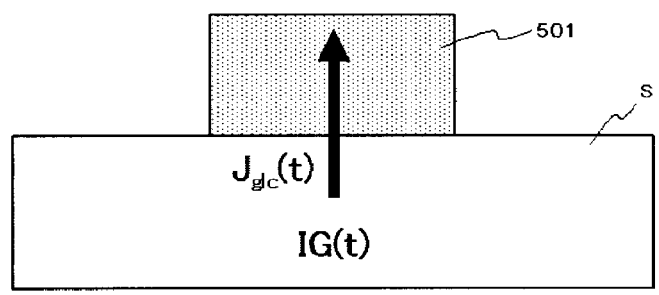
FIG. 17 is a view for illustrating a measuring principle of a blood sugar AUC value.

When the hydrogel layer 501 is fitted on the skin surface of a living body to collect an interstitial fluid from the living body through the skin as illustrated in FIG. 17, the amount of glucose collected per unit time is regarded as a glucose collecting rate [$J_{glc}$], and a glucose collecting rate at a certain time t is regarded as [$J_{glc}(t)$]. At this time, $J_{glc}(t)$ is represented as a product of a glucose concentration IG(t) in the interstitial fluid at the time t and a glucose permeability [$P_{glc}$] as shown in the following equation (3).

[Numeral Formula 3]

$$J_{glc}(t) = P_{glc} \times IG(t) \quad (3)$$

The glucose permeability [$P_{glc}$] is a coefficient indicating the permeability to glucose through the skin, and the amount of glucose collected from the skin per unit time becomes large as the glucose permeability [$P_{glc}$] is high.

Here, a case where the collection is conducted for a predetermined period of time is considered. With respect to the left side of the equation (3), $J_{glc}(t)$ is integrated over a time T, and the integrated value thereof becomes a total amount [$M_{glc}(T)$] of glucose collected in the hydrogel layer 501 from the living body within the time T. This relation is shown in the following equation (4).

[Numeral Formula 4]

$$M_{glc}(T) = \int J_{glc}(t) \quad (4)$$

For example, when the glucose collecting rate [$J_{glc}(t)$] is 10 ng/min, the total amount [$M_{glc}$] of glucose collected in the hydrogel layer for the time T=60 min is 10 ng/min×60 min=600 ng.

Figure 18:
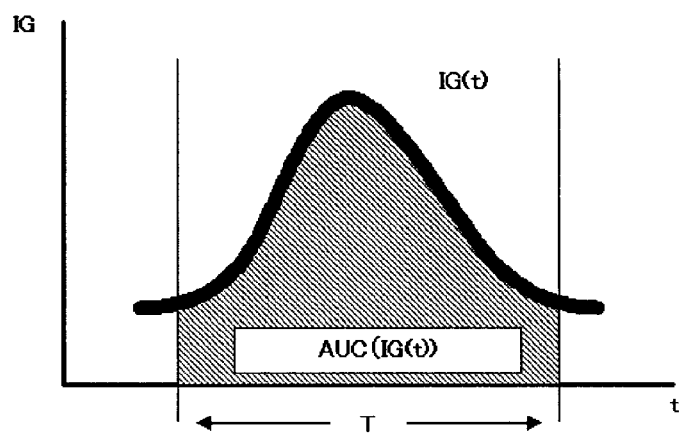
FIG. 18 is another view for illustrating the measuring principle of the blood sugar AUC value.

On the other hand, with respect to the right side of the equation (3), the glucose concentration [IG(t)] in the interstitial fluid is integrated over the time T, and the integrated value thereof becomes an area {area under the curve, AUC [IG(t)]} of a figure (a hatched portion) defined by the graph of the glucose concentration [IG(t)] for the time T as illustrated in FIG. 18. This relation is shown in the following equation (5).

[Numeral Formula 5]

$$AUC[IG(t)] = \int IG(t) \quad (5)$$

Since there is correlation between IG(t) and BG(t) as shown in the equation (5), there is also correlation between the area under the curve, AUC [IG(t)] and the area under the curve, AUC [BG(t)]. Accordingly, the relation between the area under the curve, AUC [BG(t)] and the area under the curve, AUC [IG(t)] is represented by the following equation (6) using the constant cc.

[Numeral Formula 6]

$$AUC[BG(t)] = \alpha \times AUC[IG(t)] \quad (6)$$

Here, when integration over the time T is considered, the following equation (7) is established from the equations (3) and (4).

[Numeral Formula 7]

$$M_{glc}(T) = \int P_{glc} \times IG(t) \quad (7)$$

The following equation (8) is established from the equations (5) and (7).

[Numeral Formula 8]

$$M_{glc}(T) = P_{glc} \times AUC[IG(t)] \quad (8)$$

From the equations (6) and (8), $M_{glc}(T)$ is represented by the following equation (9) using AUC[BG(T)].

[Numeral Formula 9]

$$M_{glc}(T) = (P_{glc}/\alpha) \times AUC[BG(T)] \quad (9)$$

AUC[BG(T)] can be acquired from the total amount [$M_{glc}(T)$] of glucose stored in the hydrogel layer 501 (see FIG. 17) within the time T, the permeability (glucose permeability [$P_{glc}$]) to glucose through the skin at the time T and the constant α according to the equation (9). Since the glucose concentration in the blood is almost equal to the glucose concentration in the interstitial fluid, α may be regarded as 1.

The principle of calculating out the blood sugar AUC value will hereinafter be described on the basis of the equation (1). The area under the blood sugar concentration-time curve AUC[IG(T)] determined from the glucose concentration in the interstitial fluid can be determined by the following equation (10) from the equation (9).

[Numeral Formula 10]

$$AUC[IG(T)] = M_{glc}(T)/P_{glc} \qquad (10)$$

$M_{glc}(T)$ is the amount of glucose stored in the hydrogel layer 501 within the time T. The amount of glucose stored is proportional to the glucose concentration $[C_{glc}]$ in the recovery liquid at the time glucose has been transferred to the recovery liquid from the hydrogel layer 501 so far as the volume of the recovery liquid is fixed. Accordingly, $M_{glc}(T)$ can be represented by the following equation (11) using the constants E and F.

[Numeral Formula 11]

$$M_{glc}(T) = C_{glc} \times E + F \qquad (11)$$

$P_{glc}$ indicates ease of collecting the interstitial fluid. The amount of the interstitial fluid collected varies according to the condition of the skin. The amount of glucose contained in the interstitial fluid varies depending on the blood sugar value. Accordingly, the amount of the interstitial fluid collected must be grasped. The sodium ion concentration within the body is presumed to be constant unlike glucose. When the amount of the sodium ion contained in the interstitial fluid collected is great, it is considered that the condition of the skin is in a state easy to collect the interstitial fluid. When the amount of the sodium ion collected is small on the other hand, it is considered that the condition of the skin is in a state hard to collect the interstitial fluid.

From this fact, the ease $[P_{glc}]$ of collecting the interstitial fluid can be represented by the following equation (12) using a sodium ion collecting rate J.

[Numeral Formula 12]

$$P_{glc} = J \times G + H \qquad (12)$$

Since the collecting rate J is a concentration of the sodium ion collected from the living body per unit time, the rate is represented by a value obtained by multiplying the concentration $[C_{Na}]$ of the sodium ion transferred from the hydrogel layer 501 by 1/t. Accordingly, the following equation (13) is established.

[Numeral Formula 13]

$$J = C_{Na} \times 1/t \qquad (13)$$

The following equation (14) is established from the equations (10) to (13).

[Numeral Formula 14]

$$AUC[IG(T)] = (C_{glc} \times E + F)/(C_{Na} \times 1/t) \times G + H \qquad (14)$$

The right side of this equation (14) is rearranged, thereby giving

[Numeral Formula 15]

$$AUC = (C_{Glc} \times E + F) \times t/(C_{Na} \times G + H) \qquad (1)$$

Thus, the equation (1) is drawn.

The analyzing process adaptable in the present invention comprises 3 steps of a step of forming fine passes (micropores) for interstitial fluid extraction in the skin; a step of sticking a hydrogel layer on the skin to extract an interstitial fluid; and a step of peeling the hydrogel layer stuck on the skin to assay and analyze interstitial fluid components (glucose and sodium ion) collected in the hydrogel layer.

The formation of the micropores that is the first step is conducted by pressing a micro-needle array, in which a plurality of fine projections having a height of, for example, 0.3 mm has be formed or worked, against the skin surface using a device for the exclusive use of the skin. At this time, it is necessary to clarify a position of the skin where the micropores have been formed. Thus, the exclusive device for forming the micropores is equipped with a mechanism for positioning. A tape is stuck on a portion of the device, with which the skin comes into contact, in advance. When the device is separated from the skin after the formation of the micropores, this tape for positioning is separated from the device and left on the skin. The position of the micropores formed on the skin can be specified by the tape left on the skin.

As the second step, the hydrogel layer is stuck on the skin surface matching to the tape for positioning left on the skin. The stuck state is held for 1 to 3 hours to extract and collect an interstitial fluid.

After a predetermined period of time has elapsed, analysis of interstitial fluid components that is the third step is conducted. The hydrogel layer is taken out of the skin and set in an exclusive device. This device is composed of a sodium ion measuring part and a glucose measuring part, and a value corresponding to a blood sugar AUC value can be determined from measured results thereof.

As apparent from the specific example of the biocomponent analysis unit, the analyzing process thereof and the analyzing principle thereof, the device for interstitial fluid extraction according to the present invention can be used in an analyzing process of the interstitial fluid, comprising extracting the interstitial fluid in the hydrogel layer through the skin of a vertebrate, analyzing the interstitial fluid collected in the hydrogel layer after a predetermined period of time has elapsed to measure the concentrations of a sodium ion and glucose contained therein and calculating out a value corresponding to a blood sugar AUC value in the blood of the vertebrate on the basis of these measured values.

Biocomponents are recovered from the interstitial fluid collected in the hydrogel layer using the recovery liquid and submitted for analyses of a sodium ion concentration and a glucose concentration. The analyses of the respective components can be conducted according to the above-described analyzing process. Accordingly, according to the present invention, there can be provided an analyzing process of an interstitial fluid comprising using the device for interstitial fluid extraction of the present invention in the analyzing process.

EXAMPLES

The present invention will hereinafter be described more specifically by Examples and Comparative Examples. Measuring methods or evaluating methods of various physical properties and properties are as follows.

1. Content of Sodium Ion

The content of a sodium ion in an aqueous solution of PVA used for preparation of a hydrogel layer was measured by an atomic absorption spectrometry. The sodium ion contained in the aqueous solution of PVA remains as it is.

2. Evaluation of Hydrogel Layer

The mechanical strength, hardness, resistance to water separation, water content and swelling rate of PVA hydrogel layers prepared in Examples and Comparative Examples were evaluated according to the following respective methods. The evaluation of these physical properties and properties was made in a thermohygrostat of 23° C. in temperature and 50% in relative humidity unless expressly noted.

(1) Mechanical Strength

A PVA hydrogel layer was cut into a size 7 mm wide, 12 mm long and 700 μm thick to prepare a sample. The sample was left at rest on a plane. More specifically, after the PVA hydrogel sample was left to stand for 1 minute on a polyester film left at rest in a flat state, whether change in shape by gravity occurred or not, and the hydrogel was disintegrated when the surface thereof was pressed by a finger, or not was observed to evaluate the sample as to mechanical strength according to the following standard. Three samples (n=3) of each hydrogel layer were evaluated, and a major evaluation result thereof is shown.

A: No change in shape by gravity occurred, and the gel was not disintegrated even when pressed by a finger.
B: No change in shape by gravity occurred, but the gel was disintegrated when pressed by a finger.
C: The shape of the gel was changed by gravity.

(2) Hardness

A PVA hydrogel layer was cut into a size 7 mm wide, 12 mm long and 700 μm thick to prepare a sample. The hardness of the sample was determined by measuring a penetration at 3 points on the surface of the gel by a micro-rubber hardness meter MD-1 manufactured by KOBUNSHI KEIKI CO., LTD. Three samples (n=3) of each hydrogel layer were evaluated to determine an average value thereof.

(3) Resistance to Water Separation

A PVA hydrogel layer was cut into a size 7 mm wide, 12 mm long and 700 μm thick to prepare a sample. After the PVA hydrogel sample was left to stand for 1 minute on a polyester film left at rest in a flat state, the condition of water separation was evaluated according to the following standard. Three samples (n=3) of each hydrogel layer were evaluated, and a major evaluation result thereof is shown.

A: No water separation was observed.
B: Water separation was somewhat observed on the surface of the gel.
C: Water separation was clearly observed around the gel.

(4) Water Content (% by Weight)

A PVA hydrogel layer was cut into a size 3 cm wide, 3 cm long and 700 μm thick to prepare a sample. The sample was placed on an aluminum pan, the weight of which was measured in advance, to measure the weight of the sample together with the pan. Thereafter, the sample was dried for 3 hours in a thermostat of 105° C. to measure the weight after the drying. The water content (% by weight) was determined by finding the weight (a) of the sample before the test and the weight (b) of the sample after the drying (both, g) to find the water contend (% by weight) in accordance with the following equation:

Water content(% by weight)=$[(a-b)/a]\times 100$.

Three samples (n=3) of each hydrogel layer were evaluated to determine an average value thereof.

(5) Swelling Rate (%)

A PVA hydrogel layer was cut into a size 3 cm wide, 3 cm long and 700 μm thick to prepare a sample. A value obtained by dividing the weight of the sample after immersing it in physiological saline for 24 hours by the weight of the sample before the immersion in the physiological saline was found, and the value was multiplied by 100. Three samples (n=3) of each hydrogel layer were evaluated to determine an average value thereof.

3. Evaluation of Device for Interstitial Fluid Extraction

Devices for interstitial fluid extraction prepared in Examples and Comparative Examples were evaluated as to respective items of adhesion property to the surface of the skin, pain upon peeling, adhesive deposit (adhesive residue) and irritation to the skin (irritation index).

(1) Adhesion Property to the Skin

A device for interstitial fluid extraction was stuck on the skin surface of a human forearm for 3 hours. At this time, the stack state of the device for interstitial fluid extraction on the skin surface and whether the hydrogel layer was separated from the base material layer or not were observed to evaluate the device according to the following standard (n=30).

A: The hydrogel layer and pressure sensitive adhesive layer remained adhering to the skin surface all over the surface even after the sticking for 3 hours, no vaporization of water from the hydrogel layer occurred, and the separation of the base material from the hydrogel layer is also not observed.
B: Peeling from the skin surface was partly observed in 2 to 5 samples among 30 samples.
C: Peeling from the skin surface was partly observed in at least 6 samples among 30 samples.

(2) Pain Upon Peeling

A device for interstitial fluid extraction was stuck on the skin surface of a forearm of each of 10 healthy adult persons for 3 hours. Thereafter, the device for interstitial fluid extraction was peeled from the skin surface to conduct hearing as to the degree of pain at this time. The pain upon peeling was evaluated according to the following standard.

A: At least 8 persons stated that no pain was felt, or a light pain was felt.
B: One to 3 persons stated that a pain was felt.
C: At least 4 persons stated that a pain was felt.

(3) Adhesive Deposit

Three devices for interstitial fluid extraction were stuck on the skin surface of a forearm of each of 10 healthy adult persons for 3 hours. Thereafter, the devices for interstitial fluid extraction were peeled from the skin surface to observe whether the pressure sensitive adhesive (adhesive) remained on the skin surface at this time or not (n=30). The adhesive deposit was evaluated according to the following standard.

A: No adhesive deposit was observed at all, or adhesive deposit was scarcely observed.
B: Adhesive deposit was observed in 1 to 5 devices.
C: Adhesive deposit was observed in at least 6 devices.

(4) Skin Irritation Index

Three devices for interstitial fluid extraction were stuck on the skin surface of a forearm of each of 10 healthy adult persons for 24 hours. Thereafter, the devices for interstitial fluid extraction were peeled from the skin surface. The skin irritation at the sites where the specimens were stuck after 1 hour and 24 hours from the peeling was evaluated according to the following standard (n=30)

The following −, ±, +, ++, +++ and ++++ were weighted as 0, 0.5, 1, 2, 3 and 4, respectively, to determine a skin irritation index by multiply an average value of the evaluated results of each subject by 100 in accordance with the following equation.

Judgment Standard
−: No irritation,
±: Light erythema,
+: Erythema,
++: Erythema+edema,
+++: Erythema+edema+papule,
++++: Erythema+edema+papule, serous papule, vesicle.

Skin irritation index=(Sum total of marks/the number of subjects)×100

The skin irritation index means "little irritation" for about 10, "strong irritation" for about 30 and "strongest irritation" for 50 or higher.

4. Interference in Measured Value by Sodium Ion ($Na^+$)

Whether a sodium ion contained in a hydrogel layer interfered in a measured value in the measurement of a value corresponding to a blood sugar AUC value or not was evaluated according to the following method.

A hydrogel layer was cut into a size 7 mm wide, 12 mm long and 0.7 mm thick to prepare a sample. This sample was immersed for at least 16 hours in 1,600 µl of purified water. A sodium ion concentration in the water, in which the sample had been immersed, was then measured by an ion chromatograph to convert it into a concentration of a sodium ion contained in the gel. Incidentally, in this conversion, assumption that the concentration of the sodium ion in the gel and the sodium ion concentration in the water reaches an equilibrium state is used. When the sodium ion concentration determined by the conversion is 30 ppm or less, the sodium ion is considered not to interfere in the measured value.

Example 1

1. Preparation of PVA Hydrogel Layer

Completely saponified PVA (average polymerization degree: 2,000) and potassium chloride (KCl) were added into distilled water of about 25° C., the distilled water was heated at a rate of about 10° C./min while it was being agitated by a mixer, and agitation was conducted for 1 hour at about 95° C. to prepare an aqueous solution of PVA having a PVA concentration of 14.3% by weight and a KCl concentration of 0.5% by weight.

This aqueous solution of PVA was sent to a storage tank, the internal temperature of which was set to 60° C., and left at rest for 3 hours to conduct defoaming. After the defoaming, this aqueous solution of PVA was applied on to a polyethylene film having a thickness of 35 µm and subjected to matting by means of a knife coater so as to give a thickness of 350 µm. A coating film thus formed was irradiated from above with electron beam of 300 kV in accelerating voltage at an irradiation dose of 40 kGy to crosslink PVA, thereby forming a PVA hydrogel layer. A silicone-treated polyethylene phthalate (PET) film was laminated as process paper on the hydrogel layer.

Thereafter, the aqueous solution of PVA was applied on to the hydrogel layer (first hydrogel layer), from which the process paper had been peeled, so as to give a total thickness of 700 µm, thereby foaming a coating film. This coating film was irradiated from above with the electron beam under the same conditions as described above to form a hydrogel layer (second hydrogel layer). In this manner, a PVA hydrogel layer having a thickness of 700 µm with the first and second hydrogel layers integrated was prepared. The PVA hydrogel layer was then cut into a moderate size and immersed for 30 minutes in an isotonic aqueous solution of 40° C. to the KCl concentration in the PVA solution before the irradiation of the electron beam. This process was repeated 3 times to obtain a PVA hydrogel layer of the present invention, which did substantially not contain a sodium ion.

2. Production of Device for Interstitial Fluid Extraction

An acrylic pressure sensitive adhesive was applied on to one surface of a base material of a polyethylene (PE) film having a thickness of 80 µm by a comma roll so as to give a coating weight of about 35 g/m² and dried to form a multilayer film having a layer structure of base material layer/pressure sensitive adhesive layer. Polyester film process paper subjected to a releasing treatment was laminated on the surface of the pressure sensitive adhesive layer of the multilayer film, and the resultant laminate was aged for 72 hours at ordinary temperature. The acrylic pressure sensitive adhesive is such that an alkyl acrylate copolymer of 96% by weight of isononyl acrylate and 4% by weight of acrylic acid is used as a base, and 0.03 parts by weight of an epoxy crosslinking agent is contained in 100 parts by weight of the copolymer.

The multilayer film was die-cut into a substantial square of 28 mm×28 mm, the corners of which were rounded, in such a manner that a V-shaped notch is formed in each of the opposite sides thereof, thereby preparing a pressure sensitive adhesive film. On the other hand, the hydrogel layer prepared above was die-cut into a rectangle 7 mm wide and 12 mm long to prepare a hydrogel layer for interstitial fluid extraction of a size 7 mm wide, 12 mm long and 700 µm thick. The hydrogel layer for interstitial fluid extraction was arranged on the central portion of the surface on the pressure sensitive adhesive layer side of the pressure sensitive adhesive film, and an exposed surface of the pressure sensitive adhesive layer and the surface of the hydrogel layer were then covered with a polyester film subjected to a releasing treatment to form a release layer. A device for interstitial fluid extraction having the same layer structure as that illustrated in FIGS. 5a and 5b was thereby obtained. The construction and properties of the device for interstitial fluid extraction are shown in Table 1.

Example 2

A PVA hydrogel layer and a device for interstitial fluid extraction were prepared according to the same process as in Example 1 except that the KCl concentration in the aqueous solution of PVA was changed to 3.0% by weight from 0.5% by weight. The results are shown in Table 1.

Example 3

A PVA hydrogel layer and a device for interstitial fluid extraction were prepared according to the same process as in Example 1 except that the PVA concentration and KCl concentration in the aqueous solution of PVA were changed to 12.0% by weight from 14.3% by weight and to 2.0% by weight from 0.5% by weight, respectively, and the irradiation dose was changed to 60 kGy from 40 kGy. The results are shown in Table 1.

Example 4

A PVA hydrogel layer and a device for interstitial fluid extraction were prepared according to the same process as in Example 1 except that the PVA concentration in the aqueous solution of PVA was changed to 10.0% by weight from 14.3% by weight. The results are shown in Table 1.

Example 5

A PVA hydrogel layer and a device for interstitial fluid extraction were prepared according to the same process as in Example 4 except that regarding the conditions for the irradiation of the electron beam upon the preparation of the PVA hydrogel layer, the accelerating voltage and irradiation dose were changed to 4.8 MV from 300 kV and to 20 kGy from 40 kGy, respectively. The results are shown in Table 1.

Example 6

A PVA hydrogel layer and a device for interstitial fluid extraction were prepared according to the same process as in Example 1 except that the PVA concentration in the aqueous solution of PVA was changed to 9.1% by weight from 14.3% by weight. The results are shown in Table 1.

Example 7

A PVA hydrogel layer and a device for interstitial fluid extraction were prepared according to the same process as in Example 1 except that the PVA concentration in the aqueous solution of PVA was changed to 7.7% by weight from 14.3% by weight. The results are shown in Table 1.

Example 8

A PVA hydrogel layer and a device for interstitial fluid extraction were prepared according to the same process as in Example 4 except that the PVA was changed to completely saponified PVA having an average polymerization degree of 1,700. The results are shown in Table 1.

Example 9

A PVA hydrogel layer and a device for interstitial fluid extraction were prepared according to the same process as in Example 8 except that regarding the conditions for the irradiation of the electron beam upon the preparation of the PVA hydrogel layer, the accelerating voltage and irradiation dose were changed to 4.8 MV from 300 kV and to 20 kGy from 40 kGy, respectively. The results are shown in Table 1.

Comparative Example 1

A PVA hydrogel layer and a device for interstitial fluid extraction were prepared according to the same process as in Example 1 except that the PVA concentration and KCl concentration in the aqueous solution of PVA were changed to 9.1% by weight from 14.3% by weight and to 3.0% by weight from 0.5% by weight, respectively. The results are shown in Table 2.

Comparative Example 2

A PVA hydrogel layer and a device for interstitial fluid extraction were prepared according to the same process as in Example 1 except that the PVA concentration and KCl concentration in the aqueous solution of PVA were changed to 7.7% by weight from 14.3% by weight and to 0.8% by weight from 0.5% by weight, respectively. The results are shown in Table 2.

Comparative Example 3

A PVA hydrogel layer and a device for interstitial fluid extraction were prepared according to the same process as in Example 1 except that the PVA concentration and KCl concentration in the aqueous solution of PVA were changed to 7.7% by weight from 14.3% by weight and to 1.5% by weight from 0.5% by weight, respectively. The results are shown in Table 2.

Comparative Example 4

A PVA hydrogel layer and a device for interstitial fluid extraction were prepared according to the same process as in Example 1 except that the PVA concentration and KCl concentration in the aqueous solution of PVA were changed to 7.7% by weight from 14.3% by weight and to 3.0% by weight from 0.5% by weight, respectively. The results are shown in Table 2.

Comparative Example 5

The PVA was changed to completely saponified PVA having an average polymerization degree of 1,750. In addition, the PVA concentration and KCl concentration in the aqueous solution of PVA were changed to 28.0% by weight from 14.3% by weight and to 0% by weight from 0.5% by weight, respectively. Further, the irradiation dose was changed to 60 kGy from 40 kGy. A PVA hydrogel layer and a device for interstitial fluid extraction were prepared according to the same process as in Example 1 except for these changed points. The results are shown in Table 2.

Comparative Example 6

The PVA was changed to completely saponified PVA having an average polymerization degree of 2,200. In addition, the PVA concentration and KCl concentration in the aqueous solution of PVA were changed to 16.0% by weight from 14.3% by weight and to 0% by weight from 0.5% by weight, respectively. Further, the irradiation dose was changed to 60 kGy from 40 kGy. A PVA hydrogel layer and a device for interstitial fluid extraction were prepared according to the same process as in Example 1 except for these changed points. The results are shown in Table 2.

TABLE 1

|  | Ex. 1 | Ex. 2 | Ex. 3 | Ex. 4 | Ex.. 5 | Ex. 6 | Ex.7 | Ex. 8 | Ex. 9 |
| --- | --- | --- | --- | --- | --- | --- | --- | --- | --- |
| PVA (% by weight) | 14.3 | 14.3 | 12.0 | 10.0 | 10.0 | 9.1 | 7.7 | 10.0 | 10.0 |
| KCl (% by weight) | 0.5 | 3.0 | 2.0 | 0.5 | 05 | 0.5 | 05 | 0.5 | 0.5 |
| Polymerization degree of PVA | 2000 | 2000 | 2000 | 2000 | 2000 | 2000 | 2000 | 1700 | 1700 |
| Amount of $Na^+$ | <10 ppm | <10 ppm | <10 ppm | <10 ppm | <10 ppm | <10 ppm | <10 ppm | <10 ppm | <10 ppm |
| Conditions for irradiation of EB |  |  |  |  |  |  |  |  |  |
| Accelerating voltage | 300 kV | 300 kV | 300 kV | 300 kV | 4.8 MV | 300 kV | 300 kV | 300 kV | 4.8 MV |
| Irradiation dose | 40 kGy | 40 kGy | 60 kGy | 40 kGy | 20 kGy | 40 kGy | 40 kGy | 40 kGy | 20 kGy |
| Thickness (μm) | 700 | 700 | 700 | 700 | 700 | 700 | 700 | 700 | 700 |
| Mechanical strength | A | A | A | A | A | A | A | A | A |
| Hardness | 17 | 17 | 20 | 17 | 8 | 17 | 17 | 17 | 17 |
| Resistance to water separation | A | A | A | A | A | A | A | A | A |

TABLE 1-continued

|  | Ex. 1 | Ex. 2 | Ex. 3 | Ex. 4 | Ex.. 5 | Ex. 6 | Ex.7 | Ex. 8 | Ex. 9 |
|---|---|---|---|---|---|---|---|---|---|
| Water content (%) | 86.3 | 84.7 | 86.3 | 88.8 | 88.8 | 90.9 | 91.9 | 88.4 | 88.8 |
| Swelling rate (%) | 140 | 140 | 130 | 170 | 220 | 170 | 180 | 130 | 230 |
| Adhesion property to skin | A | A | A | A | A | A | A | A | A |
| Pain upon peeling | A | A | A | A | A | A | A | A | A |
| Adhesive deposit | A | A | A | A | A | A | A | A | A |
| Skin irritation index | — | — | Gel part: 10.3 Tape part: 19.3 | — | — | — | — | — | — |
| Interference in measured value by $Na^+$ | None | None | None | None | None | None | None | None | None |

TABLE 2

|  | Comp. Ex. 1 | Comp. Ex. 2 | Comp. Ex. 3 | Comp. Ex. 4 | Comp. Ex.. 5 | Comp. Ex. 6 |
|---|---|---|---|---|---|---|
| PVA (% by weight) | 9.1 | 7.7 | 7.7 | 7.7 | 28.0 | 16.0 |
| KCl (% by weight) | 3.0 | 0.8 | 1.5 | 3.0 | 0 | 0 |
| Polymerization degree of PVA | 2000 | 2000 | 2000 | 2000 | 1750 | 2200 |
| Amount of $Na^+$ | <10 ppm | <10 ppm | <10 ppm | <10 ppm | 300 ppm | 50 ppm |
| Conditions for irradiation of EB |  |  |  |  |  |  |
| Accelerating voltage | 300 kV | 300 kV | 300 kV | 300 kV | 300 kV | 300 kV |
| Irradiation dose | 40 kGy | 40 kGy | 40 kGy | 40 kGy | 60 kGy | 60 kGy |
| Thickness (μm) | 700 | 700 | 700 | 700 | 700 | 700 |
| Mechanical strength | A | A | A | B | A | A |
| Hardness | — | — | — | — | 20 | 20 |
| Resistance to water separation | B | B | B | C | A | A |
| Water content (%) | 87.9 | 91.9 | 91.9 | 88.9 | 83.8 | 83.0 |
| Swelling rate (%) | — | — | — | — | 130 | 130 |
| Adhesion property to skin | B | B | B | C | A | A |
| Pain upon peeling | A | A | A | A | A | A |
| Adhesive deposit | A | A | A | A | A | A |
| Skin irritation index | — | — | — | — | — | — |
| Interference in measured value by $Na^+$ | None | None | None | None | Occurred | Occurred |

<Consideration>

The devices for interstitial fluid extraction according to the present invention are such that the hydrogel layer formed from the hydrophilic polymer has an area of a size that the pressure sensitive adhesive layer is exposed from around the hydrogel layer, contains at most 30 ppm of a sodium ion and causes no water separation (Examples 1 to 3). Therefore, the devices for interstitial fluid extraction according to the present invention are easy to be applied to a skin surface, inhibit irritation to the skin and can exactly analyze the concentrations of a sodium ion and glucose contained in the interstitial fluid collected.

Accordingly, the use of the device for interstitial fluid extraction according to the present invention permits extracting the interstitial fluid in the hydrogel layer through the skin of a vertebrate, analyzing the interstitial fluid collected in the hydrogel layer after a predetermined period of time has elapsed to measure the concentrations of a sodium ion and glucose contained therein and determining a value corresponding to the blood sugar AUC value in the blood of the vertebrate on the basis of these measured values.

On the other hand, the device for interstitial fluid extraction using the hydrogel layer in which water separation is observed (Comparative Examples 1 to 4), are difficult to stably extract and collect an interstitial fluid due to the water separation and also insufficient in adhesion to the skin surface.

The devices for interstitial fluid extraction using the hydrogel layer containing a relatively large amount of a sodium ion (Comparative Examples 5 and 6) cannot exactly and stably measure a value corresponding to the blood sugar AUC value because the sodium ion interferes with the measured value.

With respect to the preparation of these devices for interstitial fluid extraction of Examples and Comparative Examples, the concentration (% by weight) of PVA in the aqueous solution of PVA used in the preparation of the hydrogel layer and the osmolarity (osmole) of KCl were plotted in FIG. 19. A case where no water separation is observed and a case where water separation is observed can be distinguished by an oblique line on the basis of the resistance to water separation (whether water separation is observed or not). The case where no water separation is observed in the hydrogel layer means that the crosslinking of the hydrogel layer by irradiation of radiation is sufficient, and thus this hydrogel layer exhibits excellent performance as the hydrogel layer of the device for interstitial fluid extraction.

From FIG. 19, it is understood that when assuming that the concentration of the hydrophilic polymer is b % by weight, and the osmolarity of KCl is a osmole(s), an aqueous solution of PVA satisfying the following expression (A):

$$a \leq 0.1b - 0.6 \tag{A}$$

is used, a hydrogel layer free of water separation, even and sufficient in crosslinking by irradiation by radiation and exhibiting excellent properties is obtained. However, a is 0.05 to 0.94 osmoles, and b is 7 to 30% by weight.

FIG. 20 illustrates the results that interstitial fluid extraction rate-accelerating effects on the same skin surface in various osmolarities (osmoles) of solvents respectively using urea, glycine and KCl were determined. From the results in FIG. 20, it is understood that the interstitial fluid extraction rate-accelerating effects of urea and glycine are equivalent to KCl. From these results, it is apparent that urea and glycine can be used as the osmotic pressure control agent within an osmolarity range of from 0.05 to 0.94 osmoles in place of KCl.

FIG. 21 illustrates the results that interstitial fluid extraction rate-accelerating effects on the same skin surface in various osmolarities (osmoles) of solvents respectively using alanine, proline and KCl were determined. From the results in FIG. 21, it is understood that the interstitial fluid extraction rate-accelerating effects of alanine and proline are equivalent to KCl. From these results, it is apparent that alanine and proline can be used as the osmotic pressure control agent within an osmolarity range of from 0.05 to 0.94 osmoles in place of KCl.

INDUSTRIAL APPLICABILITY

The devices for interstitial fluid extraction according to the present invention can be used in an analyzing process of an interstitial fluid, comprising extracting the interstitial fluid in the hydrogel layer through the skin of a vertebrate, analyzing the interstitial fluid collected in the hydrogel layer after a predetermined period of time has elapsed to measure the concentrations of a sodium ion and glucose contained therein and calculating out a value corresponding to a blood sugar AUC value in the blood of the vertebrate on the basis of these measured values.

REFERENCE SIGNS LIST

1 Biocomponent analysis unit
10 Analysis unit body
20 Analyzing kit
30 Cartridge for analysis
50 Device for interstitial fluid extraction
11 Recessed part
12 Cartridge arranging part
13 Movable top plate
14 Liquid supply part
15 Liquid discharge part
21 Glucose detection part
22 Sodium detection part
23 Display part
24 Operation part
25 Control part
310 Cartridge body
311 Gel receiving part
317 Storage part for glucose detection
322 Storage part for sodium detection
330 Reaction reagents to glucose
501 Hydrogel layer
502 Pressure sensitive adhesive film
502*a* Base material
502*b* Pressure sensitive adhesive layer
503 Release layer

The invention claimed is:

1. A device for interstitial fluid extraction, comprising
(a) a base material formed from a synthetic resin film comprising a polyethylene film, a polypropylene film, a polyester film or a polyurethane film;
(b) a hydrogel layer formed from at least one hydrophilic polymer selected from the group consisting of polyvinyl alcohol and polyvinyl pyrrolidone;
(c) an adhesive layer arranged between the base material and the hydrogel layer; and
(d) a release layer, wherein
(i) the hydrogel layer has a smaller surface area than a surface area of the adhesive layer whereby a portion of a surface of the adhesive layer is exposed around the hydrogel layer, (ii) the release layer covers the exposed surface of the adhesive layer and an exposed surface of the hydrogel layer, (iii) the hydrogel layer contains not more than 30 ppm sodium ion, and (iv) the hydrogel layer exhibits no water separation when the hydrogel layer is held in a flat state for 1 minute in a thermohygrostat at 23° C. and 55% relative humidity.

2. The device for interstitial fluid extraction according to claim 1, wherein the hydrogel layer further contains an osmotic pressure control agent composed of at least one compound selected from the group consisting of potassium chloride, potassium phosphate, magnesium chloride, magnesium phosphate, calcium chloride, calcium phosphate, amino acids, urea, acetic acid, ammonia, tricine, thiamine, riboflavin, nicotinic acid amide, pyridoxine, cyanocobalamine and ascorbic acid, in a proportion providing the hydrogel layer with an osmolarity within a range of from 0.05 to 0.94 osmoles.

3. The device for interstitial fluid extraction according to claim 1, wherein the hydrogel layer is formed by irradiating a coating film of an aqueous solution of the hydrophilic polymer with radiation to crosslink the hydrophilic polymer.

4. The device for interstitial fluid extraction according to claim 1, wherein the hydrogel layer is obtained by irradiating a coating film of an aqueous solution of the hydrophilic polymer with radiation selected from the group consisting of α-ray, electron beam and γ-ray to crosslink the hydrophilic polymer, said aqueous solution having a hydrophilic polymer concentration, b, within a range of from 7 to 30% by weight, containing an osmotic pressure control agent composed of at least one compound selected from the group consisting of potassium chloride, potassium phosphate, magnesium chloride, magnesium phosphate, calcium chloride, calcium phosphate, amino acids, urea, acetic acid, ammonia, tricine, thiamine, riboflavin, nicotinic acid amide, pyridoxine, cyanocobalamine and ascorbic acid in a proportion providing the hydrogel layer with an osmolarity, a, within a range of from 0.05 to 0.94 osmoles, and containing not more than 30 ppm sodium ion, wherein
$a \leq 0.1b - 0.6$.

5. The device for interstitial fluid extraction according to claim 4, wherein the hydrogel layer is obtained by irradiating the coating film of the aqueous solution of the hydrophilic polymer with electron beam, having an accelerating voltage within a range of from 200 kV to 10 MV and an irradiation dose within a range of from 5 to 20,000 kGy, to crosslink the hydrophilic polymer.

6. The device for interstitial fluid extraction according to claim 1, wherein the hydrophilic polymer is polyvinyl alcohol having a saponification degree within a range of from 78 to 100 mol % and an average polymerization degree within a range of from 500 to 4,000.

7. The device for interstitial fluid extraction according to claim 1, wherein the water content in the hydrogel layer is within a range of from 70 to 95% by weight.

8. The device for interstitial fluid extraction according to claim 1, wherein the swelling rate of the hydrogel layer, which is obtained by multiplying a value obtained by dividing a weight after immersing the hydrogel layer in physiological saline for 24 hours by a weight before the immersion in the physiological saline by 100, is within a range of from 100 to 300%.

9. A process for analyzing an interstitial fluid, comprising contacting the hydrogel layer of the device for interstitial fluid extraction according to claim 1 with the skin of a vertebrate subjected to a permeability-improving treatment, extracting the interstitial fluid into the hydrogel layer, analyzing the interstitial fluid collected in the hydrogel layer after a predetermined period of time has elapsed to measure the concentrations of a sodium ion and glucose contained therein and calculating out a value corresponding to a glucose concentration in the blood of the vertebrate on the basis of these measured values.

10. The device for interstitial fluid extraction according to claim 1, wherein the hydrogel layer is arranged directly or through an intermediate layer composed of a nonwoven fabric or synthetic resin film on a surface of the adhesive layer.

11. The device for interstitial fluid extraction according to claim 1, wherein the adhesive layer comprises an acrylic adhesive, a rubber adhesive, a silicone adhesive or a urethane adhesive.

12. The device for interstitial fluid extraction according to claim 1, wherein the adhesive layer comprises an alkyl (meth) acrylate copolymer adhesive.

* * * * *